(12) United States Patent
Balmforth et al.

(10) Patent No.: US 10,961,569 B2
(45) Date of Patent: Mar. 30, 2021

(54) POLYNUCLEOTIDE SEQUENCE DETECTION METHOD

(71) Applicant: BIOFIDELITY LTD, Cambridge (GB)

(72) Inventors: Barnaby Balmforth, Cambridge (GB); Cameron Frayling, Cambridge (GB); Ana Silva-Weatherley, Cambridge (GB); Magdalena Stolarek-Januszkiewicz, Cambridge (GB)

(73) Assignee: BIOFIDELITY LTD, Cambridge (GB)

( * ) Notice: Subject to any disclaimer, the term of this patent is extended or adjusted under 35 U.S.C. 154(b) by 0 days.

(21) Appl. No.: 16/902,666

(22) Filed: Jun. 16, 2020

(65) Prior Publication Data

US 2020/0354786 A1    Nov. 12, 2020

Related U.S. Application Data

(63) Continuation of application No. PCT/GB2019/052017, filed on Jul. 19, 2019.

(30) Foreign Application Priority Data

Jul. 19, 2018  (EP) ..................... 18184575
Nov. 30, 2018 (WO) ................. PCT/EP2018/083227

(51) Int. Cl.
*C12Q 1/6858* (2018.01)

(52) U.S. Cl.
CPC .................... *C12Q 1/6858* (2013.01)

(58) Field of Classification Search
None
See application file for complete search history.

(56) References Cited

U.S. PATENT DOCUMENTS

| | | | |
|---|---|---|---|
| 2006/0110765 A1 | 5/2006 | Wang | |
| 2009/0239283 A1 | 9/2009 | Liu et al. | |
| 2010/0112565 A1* | 5/2010 | Tobler | C12Q 1/6848 435/6.1 |
| 2018/0080074 A1 | 3/2018 | Balmforth et al. | |

FOREIGN PATENT DOCUMENTS

| | | |
|---|---|---|
| CN | 108103159 A | 6/2018 |
| EP | 3207982 A1 | 8/2017 |
| EP | 3211092 A1 | 8/2017 |
| WO | WO 2000/49180 A1 | 8/2000 |
| WO | WO 2003/095664 A2 | 11/2003 |
| WO | WO 2014/165210 A2 | 10/2014 |
| WO | WO 2016/012789 A1 | 1/2016 |
| WO | WO 2018/210823 A1 | 11/2018 |
| WO | WO 2020/016590 A1 | 1/2020 |

OTHER PUBLICATIONS

International Search Report in International Application No. PCT/GB2019/052017, dated Sep. 30, 2019 (3 pages).
Reed, G. H. et al., "High-resolution DNA melting analysis for simple and efficient molecular diagnostics," *Pharmacogenomics*, vol. 8, pp. 597-608 (2007).
Deutscher, M. P. et al., "Enzymatic Synthesis of Deoxyribonucleic Acid," *The Journal of Biological Chemistry*, vol. 244, pp. 3019-3028 (1969).
R. Ingram et al., "PAP-LMPCR for improved, allele-specific footprinting and automated chromatin fine structure analysis," *Nucleic Acids Research*, vol. 36, No. 3, e19, pp. 1-8 (Jan. 2008).

\* cited by examiner

*Primary Examiner* — Young J Kim
(74) *Attorney, Agent, or Firm* — Bookoff McAndrews, PLLC

(57) ABSTRACT

A method of detecting a target polynucleotide sequence in a given nucleic acid analyte characterised by the steps of: a. annealing the analyte to a single-stranded probe oligonucleotide $A_0$ to create a first intermediate product which is at least partially double-stranded and in which the 3' end of $A_0$ forms a double-stranded complex with the analyte target sequence; b. pyrophosphorolysing the first intermediate product with a pyrophosphorolysing enzyme in the 3'-5' direction from the 3' end of $A_0$ to create partially digested strand $A_1$ and the analyte; c. (i) annealing $A_1$ to a single-stranded trigger oligonucleotide B and extending the $A_1$ strand in the 5'-3' direction against B; or (ii) circularising $A_1$ through ligation of its 3' and 5' ends; or (iii) ligating the 3' end of $A_1$ to the 5' end of a ligation probe oligonucleotide C; in each case to create an oligonucleotide $A_2$; d. priming $A_2$ with at least one single-stranded primer oligonucleotide and creating multiple copies of $A_2$, or a region of $A_2$; and e. detecting a signal derived from the multiple copies and inferring therefrom the presence or absence of the polynucleotide target sequence in the analyte.

26 Claims, 12 Drawing Sheets
Specification includes a Sequence Listing.

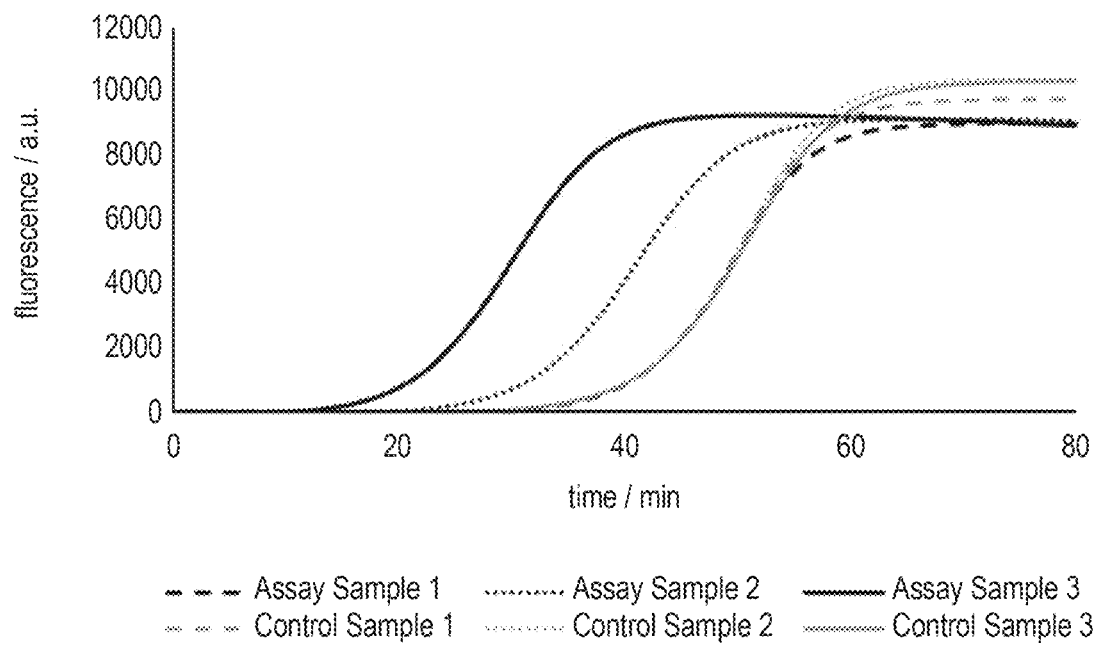
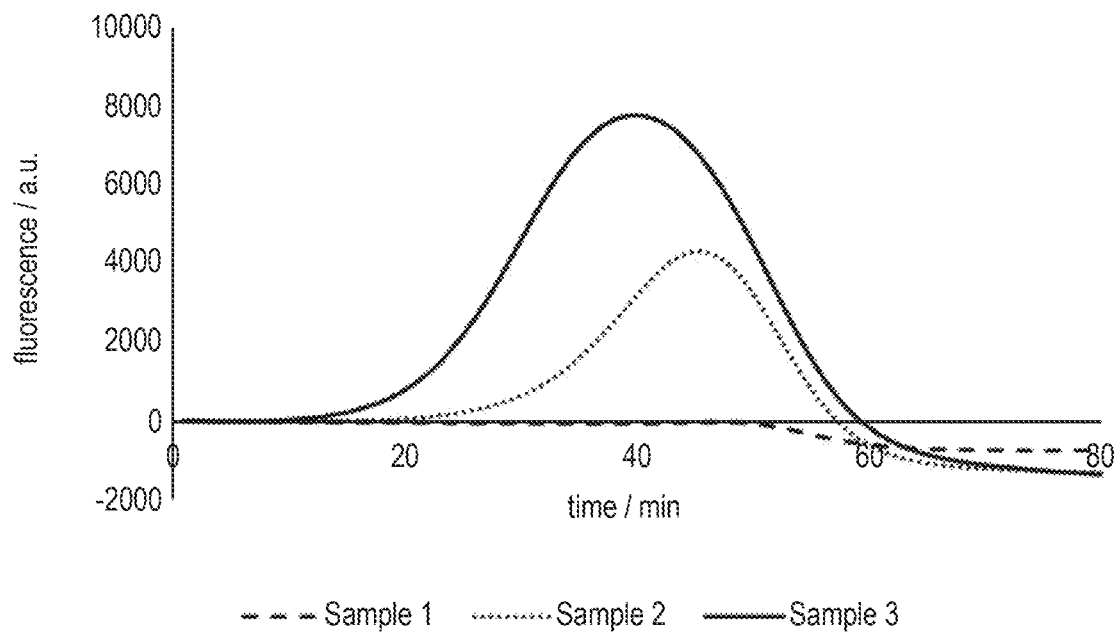
Fig. 8

SEQUENCE LISTING

<160> NUMBER OF SEQ ID NOS: 30

<210> SEQ ID NO 1
<211> LENGTH: 94
<212> TYPE: DNA
<213> ORGANISM: Artificial Sequence
<220> FEATURE:
<223> OTHER INFORMATION: example 1 a single-stranded first
    oligonucleotide 1

<400> SEQUENCE: 1
cgctcgatgt atacgctcgg accactcgta cctcgaactg tcgttagtat ttttatatgt    60
agtttctgaa gtagatatgg cagcacataa tgac    94

<210> SEQ ID NO 2
<211> LENGTH: 70
<212> TYPE: DNA
<213> ORGANISM: Artificial Sequence
<220> FEATURE:
<223> OTHER INFORMATION: example 1 a single-stranded oligonucleotide 2

<400> SEQUENCE: 2
agtacaaata tgtcattatg tgctgccata tctacttcag aaactacata taaaaatact    60
aactttaagg    70

<210> SEQ ID NO 3
<211> LENGTH: 70
<212> TYPE: DNA
<213> ORGANISM: Artificial Sequence
<220> FEATURE:
<223> OTHER INFORMATION: example 1 a single-stranded oligonucleotide 3

<400> SEQUENCE: 3
agtacaaata tctcattatg tgctgccata tctacttcag aaactacata taaaaatact    60
aactttaagg    70

<210> SEQ ID NO 4
<211> LENGTH: 70
<212> TYPE: DNA
<213> ORGANISM: Artificial Sequence
<220> FEATURE:
<223> OTHER INFORMATION: example 1 a single-stranded oligonucleotide 4

<400> SEQUENCE: 4
agtacaaata tgtcattatg agctgccata tctacttcag aaactacata taaaaatact    60
aactttaagg    70

<210> SEQ ID NO 5
<211> LENGTH: 70
<212> TYPE: DNA
<213> ORGANISM: Artificial Sequence
<220> FEATURE:
<223> OTHER INFORMATION: example 1 a single-stranded oligonucleotide 5

<400> SEQUENCE: 5
agtacaaata tgtcattatg tgctgccata actacttcag aaactacata taaaaatact    60
aactttaagg    70

<210> SEQ ID NO 6
<211> LENGTH: 70
<212> TYPE: DNA
<213> ORGANISM: Artificial Sequence
<220> FEATURE:

<223> OTHER INFORMATION: example 1 a single-stranded oligonucleotide 6

<400> SEQUENCE: 6
agtacaaata tgtcattatg tgctgccata tctacttcag taactacata taaaaatact    60
aactttaagg                                                          70

<210> SEQ ID NO 7
<211> LENGTH: 94
<212> TYPE: DNA
<213> ORGANISM: Artificial Sequence
<220> FEATURE:
<223> OTHER INFORMATION: example 2 a single-stranded oligonucleotide 1
<220> FEATURE:
<221> NAME/KEY: C at position 1 has a 5' phosphate group
<222> LOCATION: 1

<400> SEQUENCE: 7
cgctcgatgt atacgctcgg accactcgta cctcgaactg tcgttagtat ttttatatgt    60
agtttctgaa gtagatatgg cagcacataa tgac                               94

<210> SEQ ID NO 8
<211> LENGTH: 132
<212> TYPE: DNA
<213> ORGANISM: Artificial Sequence
<220> FEATURE:
<223> OTHER INFORMATION: example 2 a single-stranded oligonucleotide 2
<220> FEATURE:
<221> NAME/KEY: A at position 1 has a 5' phosphate group
<222> LOCATION: 1

<400> SEQUENCE: 8
atgttcgatg aggcacgata tagatgtacg ctttgacata cgctttgaca atacttgagc    60
agtcggcaga tataggatgt tgcaagctcc gtgagtccca caaccaata acctcgtttt    120 ttatatgtag tt                                                       132

<210> SEQ ID NO 9
<211> LENGTH: 57
<212> TYPE: DNA
<213> ORGANISM: Artificial Sequence
<220> FEATURE:
<223> OTHER INFORMATION: example 2 a single-stranded oligonucleotide 3
<220> FEATURE:
<221> NAME/KEY: C at position 57 is a 3'dideoxycytosine
<222> LOCATION: 57

<400> SEQUENCE: 9
tatcgtgcct catcgaacat aactacatat aaaaaacgag gttattggtt tgtggcc      57

<210> SEQ ID NO 10
<211> LENGTH: 20
<212> TYPE: DNA
<213> ORGANISM: Artificial Sequence
<220> FEATURE:
<223> OTHER INFORMATION: example 3 a single-stranded oligonucleotide
      primer 1

<400> SEQUENCE: 10
tgctcaagta ttgtcaaagc                                               20

<210> SEQ ID NO 11
<211> LENGTH: 20
<212> TYPE: DNA
<213> ORGANISM: Artificial Sequence
<220> FEATURE:
<223> OTHER INFORMATION: example 3 a single-stranded oligonucleotide primer 2

<400> SEQUENCE: 11
cggcagatat aggatgttgc                                                          20

<210> SEQ ID NO 12
<211> LENGTH: 40
<212> TYPE: DNA
<213> ORGANISM: Artificial Sequence
<220> FEATURE:
<223> OTHER INFORMATION: example 4 a single-stranded oligonucleotide 1
<220> FEATURE:
<221> NAME/KEY: T at position 26 is a deoxythymidine labelled with Atto
      594 dye
<222> LOCATION: 26
<220> FEATURE:
<221> NAME/KEY: T at position 27 is a deoxythymidine labelled with Atto
      594 dye
<222> LOCATION: 27
<220> FEATURE:
<221> NAME/KEY: T at position 30 is a deoxythymidine labelled with BHQ-2
      quencher
<222> LOCATION: 30

<400> SEQUENCE: 12
atgacctcgt aagccagtgt cagagtttttttc cagccgt                                    40

<210> SEQ ID NO 13
<211> LENGTH: 51
<212> TYPE: DNA
<213> ORGANISM: Artificial Sequence
<220> FEATURE:
<223> OTHER INFORMATION: example 4 a single-stranded oligonucleotide 2
<220> FEATURE:
<221> NAME/KEY: T at position 51 is an inverted 3'dT
<222> LOCATION: 51

<400> SEQUENCE: 13
ttcacacggc tggaaaaaaa ctctgacact ggcttacgag gtcattagatt                        51

<210> SEQ ID NO 14
<211> LENGTH: 78
<212> TYPE: DNA
<213> ORGANISM: Artificial Sequence
<220> FEATURE:
<223> OTHER INFORMATION: example 5 T790M
<220> FEATURE:
<221> NAME/KEY: A at position 1 has a 5' phosphate group
<222> LOCATION: 1

<400> SEQUENCE: 14
atgttcgatg agctttgaca atacttgagc acggcagata taggatgttg cgaagggcat             60
gagctgcatg atgagctg                                                            78

<210> SEQ ID NO 15
<211> LENGTH: 69
<212> TYPE: DNA
<213> ORGANISM: Artificial Sequence
<220> FEATURE:
<223> OTHER INFORMATION: example 5 C797S
<220> FEATURE:
<221> NAME/KEY: A at position 1 has a 5' phosphate group
<222> LOCATION: 1

<400> SEQUENCE: 15
atgttcgatg agctttgaca atacttgaag ctcgcagata taggatgttg cgatagtcca             60
ggaggctgc                                                                      69

```
<210> SEQ ID NO 16
<211> LENGTH: 73
<212> TYPE: DNA
<213> ORGANISM: Artificial Sequence
<220> FEATURE:
<223> OTHER INFORMATION: example 5 L861Q
<220> FEATURE:
<221> NAME/KEY: A at position 1 has a 5' phosphate group
<222> LOCATION: 1

<400> SEQUENCE: 16
atgttcgatg agctttgaca atacttgatc gatgcagata taggatgttg cgatccgcac      60
ccagctgttt ggc                                                         73

<210> SEQ ID NO 17
<211> LENGTH: 36
<212> TYPE: DNA
<213> ORGANISM: Artificial Sequence
<220> FEATURE:
<223> OTHER INFORMATION: example 5 T790M splint oligo

<400> SEQUENCE: 17
tgtcaaagct catcgaacat gcccttcgca acatct                                36

<210> SEQ ID NO 18
<211> LENGTH: 36
<212> TYPE: DNA
<213> ORGANISM: Artificial Sequence
<220> FEATURE:
<223> OTHER INFORMATION: example 5 C797S splint oligo

<400> SEQUENCE: 18
tgtcaaagct catcgaacat tcctggacta tcgcat                                36

<210> SEQ ID NO 19
<211> LENGTH: 34
<212> TYPE: DNA
<213> ORGANISM: Artificial Sequence
<220> FEATURE:
<223> OTHER INFORMATION: example 5 L861Q splint oligo

<400> SEQUENCE: 19
agctcatcga acatctgggt gcggatcgca acaa                                  34

<210> SEQ ID NO 20
<211> LENGTH: 18
<212> TYPE: DNA
<213> ORGANISM: Artificial Sequence
<220> FEATURE:
<223> OTHER INFORMATION: example 5 T790M primer

<400> SEQUENCE: 20
acatcctata tctgccgt                                                    18

<210> SEQ ID NO 21
<211> LENGTH: 20
<212> TYPE: DNA
<213> ORGANISM: Artificial Sequence
<220> FEATURE:
<223> OTHER INFORMATION: example 5 C797S primer

<400> SEQUENCE: 21
catcgaacat tcctggacta                                                  20

<210> SEQ ID NO 22
<211> LENGTH: 20
```

```
<212> TYPE: DNA
<213> ORGANISM: Artificial Sequence
<220> FEATURE:
<223> OTHER INFORMATION: example 5 L861Q primer

<400> SEQUENCE: 22
tcatcgaaca tctgggtgcg                                                   20

<210> SEQ ID NO 23
<211> LENGTH: 20
<212> TYPE: DNA
<213> ORGANISM: Artificial Sequence
<220> FEATURE:
<223> OTHER INFORMATION: example 5 universal reverse primer

<400> SEQUENCE: 23
atgttcgatg agctttgaca                                                   20

<210> SEQ ID NO 24
<211> LENGTH: 80
<212> TYPE: DNA
<213> ORGANISM: Artificial Sequence
<220> FEATURE:
<223> OTHER INFORMATION: example 8 synthetic oligonucleotide 1

<400> SEQUENCE: 24
ccgcagcatg tcaagatcac agattttggg ctggccaaac tgctgggtgc ggaagagaaa       60
gaataccatg cagaaggagg                                                   80

<210> SEQ ID NO 25
<211> LENGTH: 80
<212> TYPE: DNA
<213> ORGANISM: Artificial Sequence
<220> FEATURE:
<223> OTHER INFORMATION: example 8 synthetic 'mutant' oligonucleotide 2

<400> SEQUENCE: 25
ccgcagcatg tcaagatcac agattttggg cgggccaaac tgctgggtgc ggaagagaaa       60
gaataccatg cagaaggagg                                                   80

<210> SEQ ID NO 26
<211> LENGTH: 71
<212> TYPE: DNA
<213> ORGANISM: Artificial Sequence
<220> FEATURE:
<223> OTHER INFORMATION: example 8 assay probe oligonucleotide 3
<220> FEATURE:
<221> NAME/KEY: A at position 1 has a 5' phosphate group
<222> LOCATION: 1

<400> SEQUENCE: 26
atgttcgatg agctttgaca atacttgatc gatgcagata taggatgttg cgacagtttg       60
gcccgcccaa a                                                            71

<210> SEQ ID NO 27
<211> LENGTH: 71
<212> TYPE: DNA
<213> ORGANISM: Artificial Sequence
<220> FEATURE:
<223> OTHER INFORMATION: example 8 assay probe oligonucleotide 4
<220> FEATURE:
<221> NAME/KEY: A at position 1 has a 5' phosphate group
<222> LOCATION: 1

<400> SEQUENCE: 27
```

```
atgttcgatg agctttgaca atacttgatc gatgcagata taggatgttg cgacagtttg      60
gccggcccaa a                                                           71

<210> SEQ ID NO 28
<211> LENGTH: 36
<212> TYPE: DNA
<213> ORGANISM: Artificial Sequence
<220> FEATURE:
<223> OTHER INFORMATION: example 8 splint olignucleotide 5

<400> SEQUENCE: 28
tgtcaaagct catcgaacat gccaaactgt cgcaag                                36

<210> SEQ ID NO 29
<211> LENGTH: 20
<212> TYPE: DNA
<213> ORGANISM: Artificial Sequence
<220> FEATURE:
<223> OTHER INFORMATION: example 8 primer oligonucleotide 6

<400> SEQUENCE: 29
tcgcaacatc ctatatctgc                                                  20

<210> SEQ ID NO 30
<211> LENGTH: 20
<212> TYPE: DNA
<213> ORGANISM: Artificial Sequence
<220> FEATURE:
<223> OTHER INFORMATION: example 8 primer oligonucleotide 7

<400> SEQUENCE: 30
tgagctttga caatacttga                                                  20
```

POLYNUCLEOTIDE SEQUENCE DETECTION METHOD

CROSS-REFERENCE TO RELATED APPLICATIONS

This application is a continuation of International Application No. PCT/GB2019/052017, filed on Jul. 19, 2019, incorporated by reference herein, which claims the benefit of priority to European Application No. 18184575.1, filed on Jul. 19, 2018, and International Application No. PCT/EP2018/083227, filed on Nov. 30, 2018.

SEQUENCE LISTING

This application contains a sequence listing, submitted electronically in ASCII format under the filename Sequence Listing.txt, which is incorporated by reference herein in its entirety. The ASCII copy of the sequence listing was created on Jun. 16, 2020, and is 8,752 bytes in size.

This invention relates to an improved polynucleotide sequence detection method suitable for testing for the presence of a large number of diagnostic markers, including those used in the identification of cancer, infectious disease and transplant organ rejection. It is also useful for companion diagnostic testing in which a panel of markers must be identified reliably and at low cost.

The polymerase chain reaction (PCR) is a well-known and powerful technique for amplifying DNA or RNA present in laboratory and diagnostic samples to a point where they can be reliably detected and/or quantified. However, when applied for the purposes of investigating analyte samples containing low-levels of such molecules, it suffers from a number of limitations. First, whilst the technique can detect as little as a single target molecule, it is prone to generating false positive results due to unwanted amplification of other nucleic acid sequences present in the sample. This makes the choice of oligonucleotide primers used to initiate the reaction key; which in turn makes designing primers with the required level of specificity relatively complex. As a consequence, many PCR-based tests available on the market today have limited specificity.

A second drawback is that multiplexing of PCR-based methods is in practice limited to at most tens of target sequences (frequently no more than 10) with the avoidance of primer-primer interactions resulting in the need for relatively narrow operational windows.

Another issue is that, because the PCR reaction cycles in an exponential fashion, quantification of the target is difficult; small variations in the efficiency of the reaction having a huge impact on the amount of detectable material generated. Even with appropriate controls and calibrations in place, quantification is thus typically limited to an accuracy within a factor of around 3.

Finally, mutations in the region targeted for investigation by PCR amplification methods can have unwanted side effects. For example, there have been instances where FDA-approved tests have had to be withdrawn because the target organism underwent mutation in the genetic region targeted by the test primers resulting in large numbers of false negatives. Conversely, if a specific single nucleotide polymorphism (SNP) is targeted for amplification the PCR method will often give a false positive when the wild-type variant is present. Avoiding this requires very careful primer design and further limits the efficacy of multiplexing. This is particularly relevant when searching for panels of SNPs as is a common requirement in cancer testing/screening or companion diagnostics.

SUMMARY OF INVENTION

We have now developed a new method which builds on our experience using the pyrophosphorolysis method employed in our earlier sequencing patents (see for example WO 2016012789) to overcome many of these limitations. In doing so, it harnesses the double-strand specificity of pyrophosphorolysis; a reaction which will not proceed efficiently with single-stranded oligonucleotide substrates or double-stranded substrates which include blocking groups or nucleotide mismatches. Thus, according to the present invention, there is provided a method of detecting a target polynucleotide sequence in a given nucleic acid analyte characterised by the steps of:

a. annealing the analyte to a single-stranded probe oligonucleotide $A_0$ to create a first intermediate product which is at least partially double-stranded and in which the 3' end of $A_0$ forms a double-stranded complex with the analyte target sequence;

b. pyrophosphorolysing the first intermediate product with a pyrophosphorolysing enzyme in the 3'-5' direction from the 3' end of $A_0$ to create partially digested strand $A_1$ and the analyte;

c. (i) annealing $A_1$ to a single-stranded trigger oligonucleotide B and extending the $A_1$ strand in the 5'-3' direction against B; or (ii) circularising $A_1$ through ligation of its 3' and 5' ends; or (iii) ligating the 3' end of $A_1$ to the 5' end of a ligation probe oligonucleotide C; in each case to create an oligonucleotide $A_2$;

d. priming $A_2$ with at least one single-stranded primer oligonucleotide and creating multiple copies of $A_2$, or a region of $A_2$; and e. detecting a signal derived from the multiple copies and inferring therefrom the presence or absence of the polynucleotide target sequence in the analyte.

The analytes to which the method of the invention can be applied are those nucleic acids, such as naturally-occurring or synthetic DNA or RNA molecules, which include the target polynucleotide sequence(s) being sought. In one embodiment, the analyte will typically be present in an aqueous solution containing it and other biological material and in one embodiment the analyte will be present along with other background nucleic acid molecules which are not of interest for the purposes of the test. In some embodiments, the analyte will be present in low amounts relative to these other nucleic acid components. Preferably, for example where the analyte is derived from a biological specimen containing cellular material, prior to performing step (a) of the method some or all of these other nucleic acids and extraneous biological material will have been removed using sample-preparation techniques such as filtration, centrifuging, chromatography or electrophoresis. Suitably, the analyte is derived from a biological sample taken from a mammalian subject (especially a human patient) such as blood, plasma, sputum, urine, skin or a biopsy. In one embodiment, the biological sample will be subjected to lysis in order that the analyte is released by disrupting any cells present. In other embodiments, the analyte may already be present in free form within the sample itself; for example cell-free DNA circulating in blood or plasma.

BRIEF DESCRIPTION OF DRAWINGS

FIG. 8: (i) signal over wild-type observed in the presence of the L858R EGFR mutation from assay and control probes as described in Example 8 and (ii) the result of subtraction of the control probe signal from that of the assay probe for each sample.

In step b, the partially double-stranded first intermediate product is pyrophosphorylsed with a pyrophosphorolysing enzyme in the 3'-5' direction from the 3' end of $A_0$ to create a partially digested strand $A_1$, the analyte and the undigested $A_0$ molecule which did not anneal to a target in step a.

Figure 10:
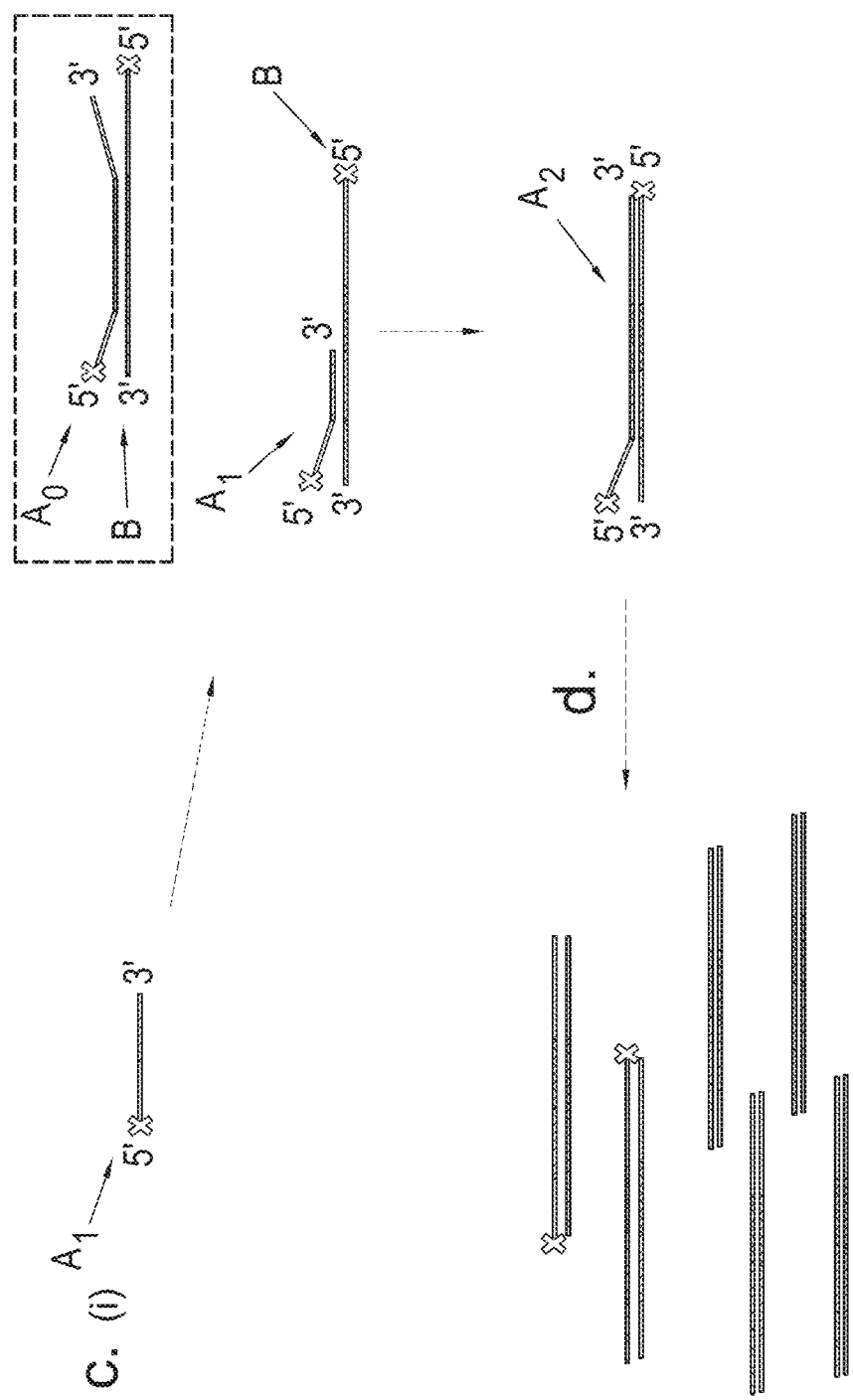

FIG. 10: One embodiment of steps c(i) and d of the method of the invention. In step c(i), $A_1$ is annealed to a single-stranded trigger oligonucleotide B and the $A_1$ strand is extended in the 5'-3' direction against B to create an oligonucleotide $A_2$. In this illustrative example, trigger oligonucleotide B has a 5' chemical block. The undigested $A_0$ from step b of the method anneals to the trigger oligonucleotide B, however it is unable to be extended in the 5'-3' direction against B to generate sequences that are the target for the amplification primers of step d.

In step d, $A_2$ is primed with at least one single-stranded primer oligonucleotide and multiple copies of $A_2$, or a region of $A_2$ are created.

Figure 11:
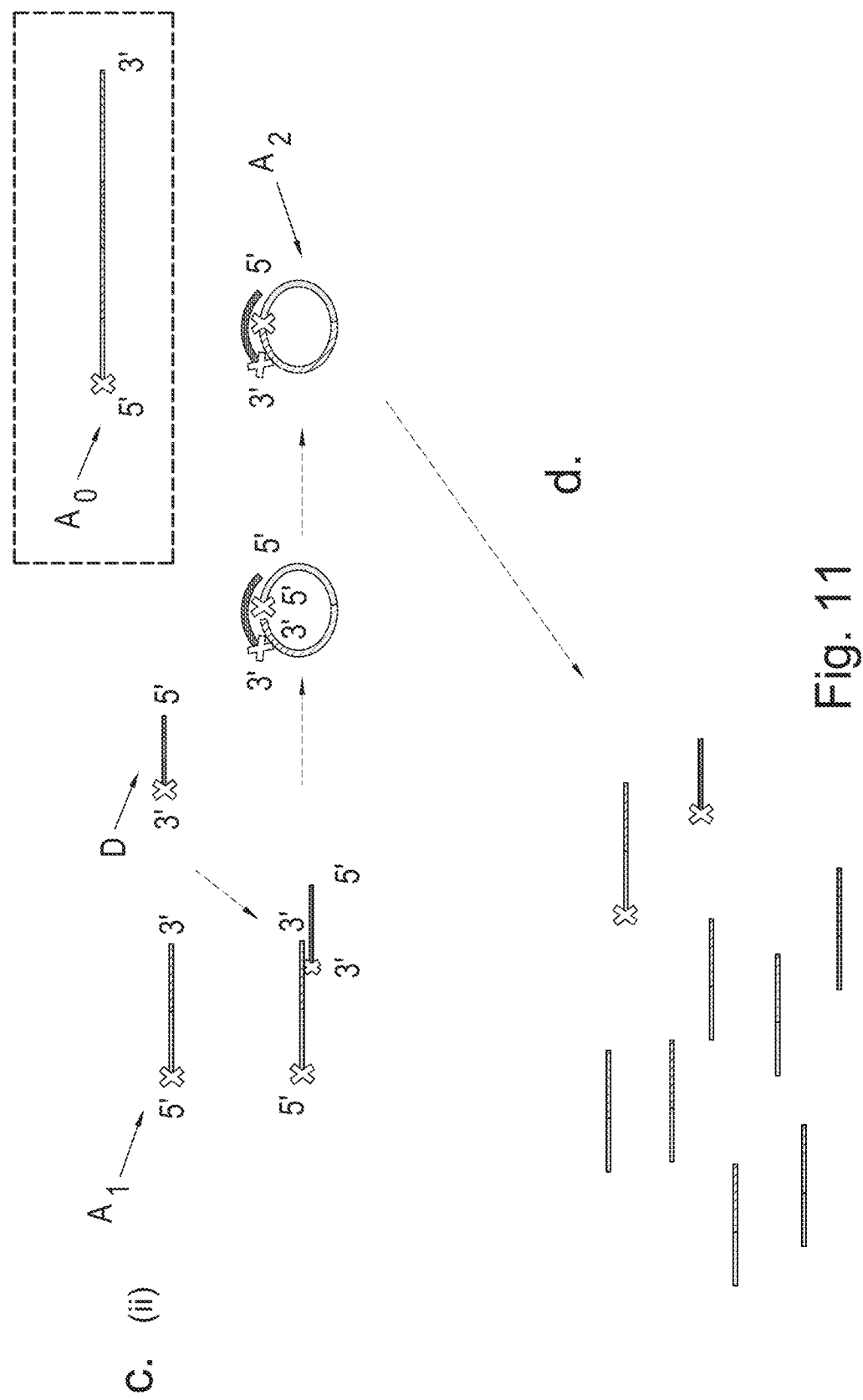

FIG. 11: One embodiment of steps c(ii) and d of the method of the invention. In step c(ii), $A_1$ is annealed to a splint oligonucleotide D, and then circularised by ligation of its 3' and 5' ends. In step d, the now circularised $A_2$ is primed with at least one single-stranded primer oligonucleotide and multiple copies of $A_2$, or a region of $A_2$ are created. In this illustrative example, the splint oligonucleotide D is unable to extend against $A_1$ by virtue of either a 3'-modification (chemical in this illustration) or through a nucleotide mismatch between the 3' end of D and the corresponding region of $A_2$.

In step d, $A_2$ is primed with at least one single-stranded primer oligonucleotide and multiple copies of $A_2$, or a region of $A_2$ are created.

Figure 12:
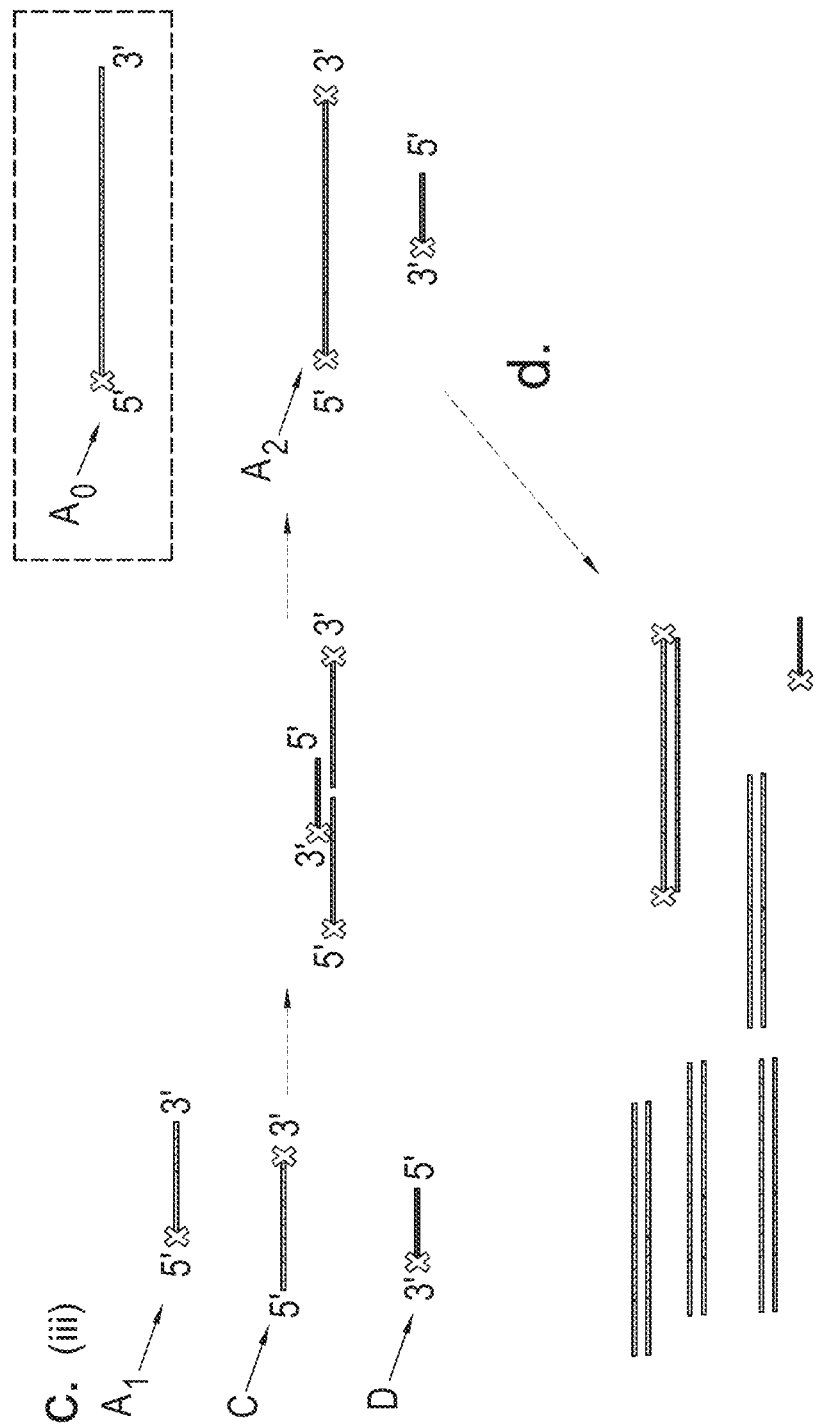

FIG. 12: One embodiment of steps c(iii) and d of the method of the invention. In step c(iii), the 3' region of a splint oligonucleotide D anneals to the 3' region of $A_1$ whilst the 5' region of the splint oligonucleotide D anneals to the 5' region of a ligation probe C. Thus, a second intermediate product $A_2$ is formed comprised of $A_1$, C and optionally an intermediate region formed by extension of $A_1$ in the 5'-3' direction to meet the 5' end of C. In this illustrative example, the ligation probe C has a 3' chemical blocking group so that a 3'-5' exonuclease can be used to digest any non-ligated $A_1$ prior to the amplification step d.

In step d, $A_2$ is primed with at least one single-stranded primer oligonucleotide and multiple copies of $A_2$, or a region of $A_2$ are created.

DESCRIPTION OF EMBODIMENTS

According to the present invention, there is provided a method of detecting a target polynucleotide sequence in a given nucleic acid analyte characterised by the steps of:
  a. annealing the analyte to a single-stranded probe oligonucleotide $A_0$ to create a first intermediate product which is at least partially double-stranded and in which the 3' end of $A_0$ forms a double-stranded complex with the analyte target sequence;
  b. pyrophosphorolysing the first intermediate product with a pyrophosphorolysing enzyme in the 3'-5' direction from the 3' end of $A_0$ to create partially digested strand $A_1$ and the analyte;
  c. (i) annealing $A_1$ to a single-stranded trigger oligonucleotide B and extending the $A_1$ strand in the 5'-3' direction against B; or (ii) circularising $A_1$ through ligation of its 3' and 5' ends; or (iii) ligating the 3' end of $A_1$ to the 5' end of a ligation probe oligonucleotide C; in each case to create an oligonucleotide $A_2$;

d. priming $A_2$ with at least one single-stranded primer oligonucleotide and creating multiple copies of $A_2$, or a region of $A_2$; and e. detecting a signal derived from the multiple copies and inferring therefrom the presence or absence of the polynucleotide target sequence in the analyte.

The analytes to which the method of the invention can be applied are those nucleic acids, such as naturally-occurring or synthetic DNA or RNA molecules, which include the target polynucleotide sequence(s) being sought. In one embodiment, the analyte will typically be present in an aqueous solution containing it and other biological material and in one embodiment the analyte will be present along with other background nucleic acid molecules which are not of interest for the purposes of the test. In some embodiments, the analyte will be present in low amounts relative to these other nucleic acid components. Preferably, for example where the analyte is derived from a biological specimen containing cellular material, prior to performing step (a) of the method some or all of these other nucleic acids and extraneous biological material will have been removed using sample-preparation techniques such as filtration, centrifuging, chromatography or electrophoresis. Suitably, the analyte is derived from a biological sample taken from a mammalian subject (especially a human patient) such as blood, plasma, sputum, urine, skin or a biopsy. In one embodiment, the biological sample will be subjected to lysis in order that the analyte is released by disrupting any cells present. In other embodiments, the analyte may already be present in free form within the sample itself; for example cell-free DNA circulating in blood or plasma.

In one embodiment, the target polynucleotide sequence in the analyte will be a gene or chromosomal region within the DNA or RNA of a cancerous tumour cell and will be characterised by the presence of one or more mutations; for example in the form of one or more single nucleotide polymorphisms (SNPs). Thus the invention will be useful in the monitoring of recurrence of disease. Patients who have been declared free of disease following treatment may be monitored over time to detect the recurrence of disease. This needs to be done non-invasively and requires sensitive detection of target sequences from blood samples. Similarly, for some cancers there are residual cancer cells that remain in a patient after treatment. Monitoring of the levels of these cells (or cell free DNA) present in the patient's blood, using the current invention, allows detection of recurrence of disease or failure of current therapy and the need to switch to an alternative.

In one embodiment, detection of the target polynucleotide sequence will allow repeated testing of patient samples during treatment of disease to allow early detection of developed resistance to therapy. For example, epidermal growth factor receptor (EGFR) inhibitors, such as gefitinib, erlotinib, are commonly used as first line treatments for non-small cell lung cancer (NSCLC). During treatment the tumour will often develop mutations in the EGFR gene (e.g T790M, C797S) which confer resistance to the treatment. Early detection of these mutations allows transfer of the patient onto alternative therapies.

In one embodiment, the target polynucleotide sequence in the analyte will be a gene or chromosomal region within the DNA or RNA of fetal origin and will be characterised by the presence of one or more mutations; for example in the form of one or more single nucleotide polymorphisms (SNPs). Thus, the invention may be used to detect mutations at very low allele fractions, at an earlier stage of pregnancy than other available testing techniques.

In another embodiment, the target polynucleotide sequence may be a gene or genomic region derived from an otherwise healthy individual but the genetic information obtained may assist in generating valuable companion diagnostic information allowing medical or therapeutic conclusions to be drawn across one or more defined groups within the human population.

In yet another embodiment, the target polynucleotide sequence may be characteristic of an infectious disease; for example a polynucleotide sequence characteristic of a gene or chromosomal region of a bacterium or a virus.

In one embodiment, the target polynucleotide sequence may be characteristic of donor DNA. When a transplanted organ is rejected by the patient, the DNA from this organ is shed into the patient's bloodstream. Early detection of this DNA would allow early detection of rejection. This could be achieved using custom panels of donor-specific markers, or by using panels of variants known to be common in the population, some of which will be present in the donor and some in the recipient. Routine monitoring of organ recipients over time is thus enabled by the claimed method.

In yet another embodiment, various versions of the method using different combinations of probe and trigger oligonucleotides (see below) are employed in parallel so that the analyte can be simultaneously screened for multiple target sequences; for example sources of cancer, cancer indicators or multiple sources of infection. In this approach, the amplified products obtained in step (d) by parallel application of the method are contacted with a detection panel comprised of one or more oligonucleotide binding dyes or sequence specific molecular probes such as a molecular beacon, hairpin probe or the like. Thus, in another aspect of the invention there is provided the use of at least one probe and optionally one trigger oligonucleotide defined below in combination with one or more chemical and biological probes selective for the target polynucleotide sequences or with the use of sequencing to identify the amplified probe regions.

Step (a) of the method of the invention comprises annealing the analyte whose presence in a given sample is being sought with a single-stranded probe oligonucleotide $A_0$. In one embodiment this oligonucleotide comprises a priming region and a 3' end which is complementary to the target polynucleotide sequence to be detected. By this means, a first intermediate product is created which is at least partially double-stranded. In one embodiment, this step is carried out in the presence of excess $A_0$ and in an aqueous medium containing the analyte and any other nucleic acid molecules.

In one embodiment, where molecular probes are to be used for detection in step (e), the probe oligonucleotide $A_0$ is configured to include an oligonucleotide identification region on the 5' side of the region complementary to the target sequence, and the molecular probes employed are designed to anneal to this identification region. In one embodiment, only the complementary region of $A_0$ is able to anneal to the target; i.e. any other regions lack sufficient complementarity with the analyte for a stable duplex to exist at the temperature at which step (b) is carried out. Here and throughout, by the term 'sufficient complementarity' is meant that, to the extent that a given region has complementarity with a given region on the analyte, the region of complementarity is more than 10 nucleotides long.

In one preferable embodiment, the 5' end of $A_0$ or an internal site on the 5' side of the priming region is rendered resistant to exonucleolysis. By this means and after step (b), an exonuclease having 5'-3' exonucleolytic activity can optionally be added to the reaction medium for the purpose of digesting any other nucleic acid molecules present whilst leaving $A_0$ and any material comprising the partially digested strand $A_1$ intact. Suitably, this resistance to exonucleolysis is achieved by introducing one or more blocking groups into the oligonucleotide $A_0$ at the required point. In one embodiment, these blocking groups may be selected from phosphorothioate linkages and other backbone modifications commonly used in the art, C3 spacers, phosphate groups, modified bases and the like. In yet another, $A_0$ has an oligonucleotide flap mismatch with respect to either or both of the 3' and 5' ends of the trigger oligonucleotide further described below.

In one embodiment, the identification region will comprise or have embedded within a barcoding region which has a unique sequence and is adapted to be indirectly identified in step (e) using a sequence-specific molecular probe applied to the amplified components $A_2$ or directly by the sequencing of these components. Examples of molecular probes which may be used include, but are not limited to, molecular beacons, TaqMan® probes, Scorpion® probes and the like.

In step (b) of the method, the double-stranded region of the first intermediate product is pyrophosphorolysed in the 3'-5' direction from the 3' end of its $A_0$ strand. As a consequence, the $A_0$ strand is progressively digested to create a partially digested strand; hereinafter referred to as $A_1$. Where the probe oligonucleotide erroneously hybridises with a non-target sequence, the pyrophosphorolysis reaction will stop at any mismatches, preventing subsequent steps of the method from proceeding. In another embodiment, this digestion continues until $A_1$ lacks sufficient complementarity with the analyte or a target region therein to form a stable duplex. At this point, the various strands then separate by melting, thereby producing $A_1$ in single-stranded form. Under typical pyrophosphorolysis conditions, this separation occurs when there are between 6 and 20 complementary nucleotides between the analyte and $A_0$.

Suitably, pyrophosphorolysis step (b) is carried out in the reaction medium at a temperature in the range 20 to 90° C. in the presence of a polymerase exhibiting pyrophosphorolysis activity and a source of pyrophosphate ion. Further information about the pyrophosphorolysis reaction as applied to the digestion of polynucleotides can be found for example in J. Biol. Chem. 244 (1969) pp. 3019-3028 or our earlier patent applications.

In one embodiment, the pyrophosphorolysis step (b) is driven by the presence of a source of excess polypyrophosphate, suitable sources include those compounds containing 3 or more phosphorous atoms.

In one embodiment, the pyrophosphorolysis step (b) is driven by the presence of a source of excess modified pyrophosphate. Suitable modified pyrophosphates include those with other atoms or groups substituted in place of the bridging oxygen, or pyrophosphate (or poly-pyrophosphate) with substitutions or modifying groups on the other oxygens. The person skilled in the art will understand that there are many such examples of modified pyrophosphate which would be suitable for use in the current invention, a non-limiting selection of which are:

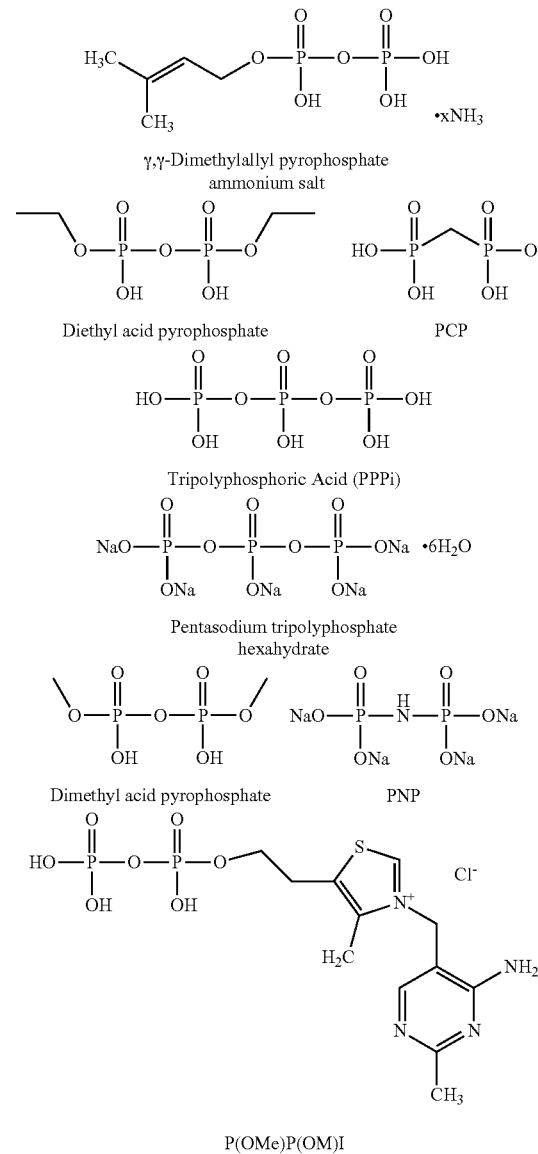

In one preferred embodiment, the source of pyrophosphate ion is PNP, PCP or Tripolyphoshoric Acid (PPPi).

Further, but not limiting, examples of sources of pyrophosphate ion for use in the pyrophosphorolysis step (b) may be found in WO2014/165210 and WO00/49180.

In one embodiment, the source of excess modified pyrophosphate can be represented as Y—H wherein Y corresponds to the general formula $(X—O)_2P(=B)—(Z—P(=B)(O—X))_n$— wherein n is an integer from 1 to 4; each Z— is selected independently from —O—, —NH— or —CH$_2$—; each B is independently either O or S; the X groups are independently selected from —H, —Na, —K, alkyl, alkenyl, or a heterocyclic group with the proviso that when both Z and B correspond to —O— and when n is 1 at least one X group is not H In one embodiment, Y corresponds to the general formula $(X—O)_2P(=B)—(Z—P(=B)(O—X))_n$— wherein n is 1, 2, 3 or 4. In another embodiment, the Y group corresponds to the general formula $(X—O)_2P(=O)—Z—P(=O)(O—H)$— wherein one of the X groups is —H. In yet another preferred embodiment, Y corresponds to the general formula (X—O)₂P(=O)—Z—P(=O)(O—X)— wherein at least one of the X groups is selected from methyl, ethyl, allyl or dimethylallyl. In an alternative embodiment, Y corresponds to either of the general formulae (H—O)₂P(=O)—Z—P(=O)(O—H)— wherein Z is either —NH— or —CH₂— or (X—O)₂P(=O)—Z—P(=O)(O—X)— wherein the X groups are all either —Na or —K and Z is either —NH— or —CH₂—.

In another embodiment, Y corresponds to the general formula (H—O)₂P(=B)—O—P(=B)(O—H)— wherein each B group is independently either O or S, with at least one being S.

Specific examples of preferred embodiments of Y include those of the formula (X1-O)(HO)P(=O)—Z—P(=O)(O—X2) wherein Z is O, NH or CH₂ and (a) X1 is γ,γ-dimethylallyl, and X2 is —H; or (b) X1 and X2 are both methyl; or (c) X1 and X2 are both ethyl; or (d) X1 is methyl and X2 is ethyl or vice versa.

In one embodiment, step (b) is carried out in the presence of a phosphatase enzyme to continually remove by hydrolysis the nucleoside triphosphates produced by the pyrophosphorolysis reaction. In another embodiment, a pyrophosphatase enzyme is added after step (b) to hydrolyse any residual pyrophosphate ion thereby ensuring that no further pyrophosphorolysis can occur in later steps. In another embodiment, step (a) and (b) are iterated so that multiple copies of $A_1$ are created from each target molecule. This may occur before or whilst the subsequent steps are being carried out. When combined with the amplification in step (d) this iteration leads to a further improvement in the sensitivity and reliability of the method and, by introducing an initial linear amplification, allows more accurate quantification of the target polynucleotide.

In one preferred, but non-essential, embodiment, at the end of step (b) or before or after step (c) an intermediate step is introduced in which an exonuclease having 5'-3' directional activity is added for the purpose of ensuring that any residual nucleic acid material present, other than that comprised of the $A_0$ or $A_1$ strands (in which the 5' blocking group is present), is destroyed. In another embodiment, this exonuclease is deactivated prior to step (d) be carried out. In yet another embodiment, prior to or whilst carrying out this exonucleolysis, all of the nucleic acid material present is phosphorylated at its 5' ends using, for example a kinase and a phosphate donor such as ATP to produce a phosphorylated end site required for initiating the exonucleolysis by certain types of 5'-3' exonucleases.

After step (b), or where relevant the intermediate step mentioned above, $A_1$ is, in one embodiment (i), annealed to a single-stranded trigger oligonucleotide B to create a second intermediate product which is also partially double-stranded. In one embodiment, B is comprised of an oligonucleotide region complementary to the 3' end of $A_1$ with a flanking oligonucleotide region at its 5' end which is not substantially complementary to $A_0$. Here and throughout, by the term 'not substantially complementary to' or equivalent wording is meant that to the extent that a given flanking region has complementarity with a given region on $A_0$, the region of complementarity is less than 10 nucleotides long. Thereafter, in step (c) the $A_1$ strand of this second intermediate product is extended in the 5'-3' direction to create a third intermediate product, comprised of B and extended $A_1$ strand (hereinafter referred to as $A_2$).

In another embodiment, B comprises (i) an oligonucleotide region complementary to the 3' end of $A_1$; (ii) an oligonucleotide region complementary to the 5' end of $A_1$ and optionally (iii) an intermediate oligonucleotide region between these two regions and wherein B is unable to undergo extension against $A_1$ through the presence of either one or more nucleotide mismatches or a chemical modification at its 3' end. In another embodiment, B is modified both at its 3' end and internally to prevent other oligonucleotides being extended against it.

In both these embodiments, B is suitably comprised of oligonucleotide regions which are each independently up to 150 nucleotides, typically 5 to 100 nucleotides and most preferably 10 to 75 nucleotides long. In one embodiment, all the regions of B independently have a length in the range 10 to 50 nucleotides. In another preferred embodiment, the 5' end of B or a region adjacent thereto is also protected with a blocking group of the type mentioned above to make it resistant to exonucleolysis. In some embodiments, the 5' end of B is folded back on itself to create a double-stranded hairpin region. In yet another embodiment, both the 3' and 5' ends of B have one or more nucleotide mismatches with respect to the ends of its $A_1$ counterpart strand.

In another embodiment, step (c) alternatively comprises (ii) ligating the two ends of $A_1$ together in the presence of a ligase to create a third intermediate product in which the $A_1$ strand is not extended but rather circularised. This ligation is typically carried out through the addition of a splint oligonucleotide D, having regions complementary to the 3' and 5' ends of $A_1$ such that, when annealed to D, the 3' and 5' ends of $A_1$ form a nick which can be ligated or a gap which can be filled prior to subsequent ligation. In this embodiment, circularised $A_1$ in effect becomes $A_2$ for the purpose of subsequent steps. In another embodiment, the $A_1$ strand is still extended in the 5'-3' direction, using a polymerase lacking in 5'-3' exonuclease and strand-displacement activity, and is then circularised so that this extended and circularised product in effect becomes $A_2$. In another embodiment, the 3' and 5' ends of $A_1$, or extended $A_1$ are joined together by a bridging-group which may not necessarily include an oligonucleotide region.

In the case where the third intermediate product comprises an $A_2$ strand which is circularised, it is advantageous to treat the reaction mixture generated in step (c) with an exonuclease or combination of exonucleases to digest any residual nucleic acid components which are not circularised. Thereafter, in another embodiment the exonuclease is deactivated prior to step (d) taking place.

In another embodiment (iii), step (c) is carried out in the presence of a ligation probe C having a 5' region complementary to at least part of a 5' end region of a splint oligonucleotide D or to the target oligonucleotide, a ligase, and optionally a polymerase lacking both a strand displacement capability and 5'-3' directional exonuclease activity. By such means, a second intermediate product is formed in which the $A_2$ strand is comprised of $A_1$, C and optionally an intermediate region formed by extension of $A_1$ in the 5'-3' direction to meet the 5' end of C. In such an embodiment, the primers employed in step (d) (see below) are chosen to amplify at least a region of $A_2$ including the site at which ligation of the $A_1$ to C has occurred. In this embodiment, we have found that it is advantageous to include a 3' blocking group on C so that a 3'-5' exonuclease can be used to digest any non-ligated $A_1$ prior to amplification. Suitable polymerases which may be used include but are not limited to Hemo KlenTaq, Mako and Stoffel Fragment.

In one embodiment, where steps c(ii) or c(iii) are employed $A_1$ is optionally extended in 5'-3' direction prior to ligation. In one embodiment this optional extension and the ligation are performed against the target oligonucleotide, while in another embodiment they are performed through addition of a further splint oligonucleotide D to which $A_1$ anneals prior to extension and/or ligation. In one embodiment, D comprises an oligonucleotide region complementary to the 3' end of $A_1$ and a region complementary to either the 5' end of oligonucleotide C or to the 5' end of $A_1$. In another embodiment, D is unable to extend against $A_1$ by virtue of either a 3'-end modification or through a nucleotide mismatch between the 3' end of D and the corresponding region of $A_1$.

In subsequent step (d), the $A_2$ strand or a desired region thereof is caused to undergo amplification so that multiple, typically many millions, of copies are made. This is achieved by priming a region of $A_2$ and subsequently any amplicons derived therefrom with single-stranded primer oligonucleotides, provided for example in the form of a forward/reverse or sense/antisense pair, which can anneal to a complementary region thereon. The primed strand then becomes the point of origin for amplification. Amplification methods include, but are not limited to, thermal cycling and isothermal methods such as the polymerase chain reaction, recombinase polymerase amplification and rolling circle amplification; the last of these being applicable when $A_2$ is circularised. By any of these means, many amplicon copies of $A_2$ and in some instances its sequence complement can be rapidly created. The exact methodologies for performing any of these amplification methods will be well-known to one of ordinary skill and the exact conditions and temperature regimes employed are readily available in the general literature to which the reader is directed. Specifically, in the case of the polymerase chain reaction (PCR), the methodology generally comprises extending the primer oligonucleotide against the $A_2$ strand in the 5'-3' direction using a polymerase and a source of the various single nucleoside triphosphates until a complementary strand is produced; dehybridising the double-stranded product produced to regenerate the $A_2$ strand and the complementary strand; re-priming the $A_2$ strand and any of its amplicons and thereafter repeating these extension/dehybridisation/repriming steps multiple times to build-up a concentration of $A_2$ amplicons to a level where they can be reliably detected.

Finally, in step, (e) the amplicons are detected and the information obtained used to infer whether the polynucleotide target sequence is present or absent in the original analyte and/or a property associated therewith. For example, by this means a target sequence characteristic of a cancerous tumour cell may be detected with reference to specific SNPs being looked for. In another embodiment, a target sequence characteristic of the genome of a virus of bacterium (including new mutations thereof) may be detected. Many methods of detecting the amplicons or identification regions can be employed including for example an oligonucleotide binding dye, a sequence-specific molecular probe such as fluorescently-labelled molecular beacon or hairpin probe. Alternatively, direct sequencing of the $A_2$ amplicons can be performed using one of the direct sequencing methods employed or reported in the art. Where oligonucleotide binding dyes, fluorescently labelled beacons or probes are employed it is convenient to detect the amplicons using an arrangement comprising a source of stimulating electromagnetic radiation (laser, LED, lamp etc.) and a photodetector arranged to detect emitted fluorescent light and to generate therefrom a signal comprising a data stream which can be analysed by a microprocessor or a computer using specifically-designed algorithms.

In one specific manifestation of the invention, multiple $A_0$ probes are employed each selective for a different target sequence and each including an identification region. In one embodiment, the region amplified in step (d) then includes this identification region. In another embodiment, the amplicons generated in step (d) are then inferred through detection of the identification region(s). Identification can then comprise using molecular probes or sequencing methods for example Sanger sequencing, Illumina® sequencing or one of the methods we have previously described. In another manifestation, prior to step (a) the analyte is split into multiple reaction volumes with each volume having a different probe oligonucleotide $A_0$ or plurality thereof designed to detect different target sequence(s). In another preferred embodiment, the different probes $A_0$ comprise a common priming site allowing a single or single set of primers to be used for amplification step (d).

In some embodiments, the amplification step (d) may be carried out by standard polymerase chain reaction (PCR) or through isothermal amplification such as rolling circle amplification (RCA). In some embodiments, the RCA may be in the form of exponential RCA for example hyperbranched RCA, which can result in double-stranded DNA of a variety of different lengths. In some embodiments, it may be desirable to provide different probes that can produce different products with different lengths.

In some embodiments, step (e) further comprises the steps of:
i. labelling the multiple copies of $A_2$, or a region of $A_2$ using one or more oligonucleotide fluorescent binding dyes or molecular probes;
ii. measuring the fluorescent signal of the multiple copies;
iii. exposing the multiple copies to a set of denaturing conditions; and
iv. identifying the polynucleotide target sequence in the analyte by monitoring changes in the fluorescent signal of the multiple copies during exposure to the denaturing conditions.

In some embodiments, step (e) may take the form of detection and analysis using melting curve analysis. Melting curve analysis can be an assessment of the dissociation characteristics of double-stranded DNA during heating. The temperature at which 50% of DNA in a sample is denatured into two separate stands is known as the melting temperature (Tm). As the temperature is raised, the double strand begins to dissociate, with different molecules of double-stranded DNA dissociating at different temperatures based on composition (a G-C base pairing has 3 hydrogen bonds compared to only 2 between A-T—thus a higher temperature is required to separate a G-C than an A-T), length (a longer length of double stranded DNA with more hydrogen bonds will require a higher temperature to fully dissociate into two separate single strands than one that is shorter) and complementarity (a DNA molecule with a large number of mismatches will have a lower Tm by nature of containing fewer hydrogen bonds between matching base pairs).

In some embodiments, the amplification step (d) may be carried out in the presence of an intercalating fluorescent agent. Thus, when the melting curve analysis is performed, changes in fluorescence are monitored, indicating the Tm (and so identity) of the reaction product and hence the target polynucleotide sequence. Changes in fluorescence can be detected using an arrangement comprising a source of stimulating electromagnetic radiation (laser, LED, lamp etc.) and a photodetector arranged to detect emitted fluorescent light and to generate therefrom a signal comprising a data stream which can be analysed by a microprocessor or a computer using specifically-designed algorithms.

The intercalating fluorescent agent may be dye specific to double-stranded DNA, such as SYBR green, EvaGreen, LG Green, LC Green Plus, ResoLight, Chromofy or SYTO 9. The person skilled in the art will appreciate there are many intercalating fluorescent agents which could be used in the current invention and the above list is not intended to limit the scope of the current invention. The intercalating fluorescent agent may be a fluorescently labelled DNA probe. In one embodiment of the invention, juxtapositioned probes, one comprising a fluorophore, the other a suitable quencher, can be used to determine the complementarity of the DNA probe to a target amplified sequence.

In another aspect of the invention, there is provided a method of identifying a target polynucleotide sequence in a given nucleic acid analyte characterised by the steps of:
a. annealing a nucleic acid analyte to a single-stranded probe oligonucleotide $A_0$ to create a first intermediate product which is at least partially double-stranded and in which the 3' end of $A_0$ forms a double-stranded complex with the analyte target sequence;
b. pyrophosphorolysing the first intermediate product with a pyrophosphorolysing enzyme in the 3'-5' direction from the 3' end of $A_0$ to create partially digested strand $A_1$ and the analyte;
c. (i) annealing $A_1$ to a single-stranded trigger oligonucleotide B and extending the $A_1$ strand in the 5'-3' direction against B; or (ii) circularising $A_1$ through ligation of its 3' and 5' ends; or (iii) ligating the 3' end of $A_1$ to the 5' end of a ligation probe oligonucleotide C; in each case to create an oligonucleotide $A_2$;
d. priming $A_2$ with at least one single-stranded primer oligonucleotide and creating multiple copies of $A_2$, or a region of $A_2$.
e. labelling the multiple copies of $A_2$, or a region of $A_2$ using one or more oligonucleotide fluorescent binding dyes or molecular probes;
f. measuring the fluorescent signal of the multiple copies;
g. exposing the multiple copies to a set of denaturing conditions; and
h. identifying the target polynucleotide sequence by monitoring a change in the fluorescent signal of the multiple copies during exposure to the denaturing conditions.

In some embodiments, the denaturing conditions may be provided by varying the temperature e.g. increasing the temperature to a point where the double strand begins to dissociate. Additionally or alternatively, the denaturing conditions may also be provided by varying the pH such that the conditions are acidic or alkaline, or by adding in additives or agents such as a strong acid or base, a concentrated inorganic salt or organic solvent e.g. alcohol.

In a further aspect of the invention, which may be employed in association with the method of the first aspect or on a stand-alone basis, the analyte in single-stranded form may be prepared from the biological sample mentioned above by a series of preliminary steps designed to amplify the analyte and separate if from the background genomic DNA which is typically present in significant excess. This method is generally applicable to the production of single-stranded target analytes and is therefore useful in situations other than when it is integrated with or further comprises part of the method of the first aspect of the invention. Accordingly, there is provided a method for preparing at least one single-stranded analyte of a nucleic acid comprised of a target polynucleotide region characterised by the steps of (i) producing amplicons of the analyte(s) by subjecting a biological sample comprised of corresponding double-stranded versions of the analyte(s) and optionally background genomic DNA to cycles of amplification. In one preferred embodiment amplification is carried out using the polymerase chain reaction (PCR) in the presence of a polymerase, nucleoside triphosphates and at least one corresponding primer pair wherein one of the primers includes a 5'-3' exonuclease blocking group and (ii) optionally digesting the product of step (i) with an exonuclease having 5'-3' exonucleolytic activity. In one embodiment, the method may further comprise (iii) reacting the product of step (ii) with a proteinase to destroy the polymerase and thereafter (iv) deactivating the proteinase by heating the product of step (iii) to a temperature in excess of 50° C.

In one preferred embodiment steps (i) to (iv) are carried out prior to step (1) of the method of the first aspect of the invention to produce an integrated method of detecting target sequences derived from a biological sample. In another embodiment, the biological sample has undergone cell lysis before step (i) is carried out.

In one embodiment of step (i) the nucleoside triphosphates are a mixture of the four deoxynucleoside triphosphates characteristic of naturally occurring DNA. In a preferred embodiment the mixture of deoxynucleoside triphosphates comprise deoxyuridine triphosphate (dUTP) instead of deoxythymidine triphosphate (dTTP) and step (i) is further carried out in the presence of the enzyme dUTP-DNA glycolase (UDG) to remove any contaminating amplicons from previous assays. In yet another embodiment, a high fidelity polymerase is used in step (i) for example one of those sold under the trade name Phusion® or Q5.

In one embodiment, step (i) is carried out using a limited amount of primer and an excess of amplification cycles. By this means a fixed amount of amplicons is produced regardless of the initial amount of analyte. Thus the need for analyte quantification prior to subsequent steps is avoided. In another embodiment of step (i), which has the advantage of obviating the need for step (ii), amplification is carried out in the presence of a primer pair where one of the two primers is present in excess of the other, resulting in generation of single-stranded amplicons once one primer is fully utilised.

In one preferred embodiment of step (ii), the 5' primer is blocked with an exonuclease blocking group selected from phosphorothioate linkages, inverted bases, DNA spacers and other oligonucleotide modifications commonly known in the art. In another embodiment the other primer in the pair has a phosphate group at its 5'-end.

In one embodiment, in step (iii) the proteinase employed is proteinase K and step (iv) is carried out by heating to a temperature of 80 to 95° C. for up to 30 minutes. In another embodiment at some point after step (ii) but before step (b) the reaction medium is treated with apyrase or other phosphatase to remove any residual nucleoside triphosphates which may be present.

In a further aspect of the invention there is provided an alternate embodiment in which the phosphorolysis step (b) is replaced with an exonuclease digestion step using a double-strand specific exonuclease. The person skilled in the art will understand that double-strand specific exonucleases include those that read in the 3'-5' direction, such as ExoIII, and those that read in the 5'-3' direction, such as Lambda Exo, amongst many others.

In one embodiment of this aspect, the double strand-specific exonuclease of step (b) proceeds in the 3'-5' direction. In such embodiments the method of the invention is characterised by the steps of:
a. annealing the analyte to a single-stranded probe oligonucleotide $A_0$ to create a first intermediate product which is at least partially double-stranded and in which the 3' end of $A_0$ forms a double-stranded complex with the analyte target sequence;
b. digesting the first intermediate product with a double-strand specific exonuclease in the 3'-5' direction from the 3' end of the $A_0$ to create partially digested strand $A_1$ and the analyte;
c. (i) annealing $A_1$ to a single-stranded trigger oligonucleotide B and extending the $A_1$ strand in the 5'-3' direction against B; or (ii) circularising $A_1$ through ligation of its 3' and 5' ends; or (iii) ligating the 3' end of $A_1$ to the 5' end of a ligation probe oligonucleotide C; in each case to create an oligonucleotide $A_2$;
d. priming $A_2$ with at least one single-stranded primer oligonucleotide and creating multiple copies of $A_2$, or a region of $A_2$; and
e. detecting a signal derived from the multiple copies and inferring therefrom the presence or absence of the polynucleotide target sequence in the analyte.

In one embodiment of this aspect, the double strand-specific exonuclease of step (b) proceeds in the 5'-3' direction. In such embodiment the method of the invention is characterised by the steps of:
a. annealing the analyte to a single-stranded probe oligonucleotide $A_0$ to create a first intermediate product which is at least partially double-stranded and in which the 5' end of $A_0$ forms a double-stranded complex with the analyte target sequence;
b. digesting the first intermediate product with a double strand-specific exonuclease in the 5'-3' direction from the 5' end of the $A_0$ to create partially digested strand $A_1$ and the analyte;
c. (i) annealing $A_1$ to a single-stranded trigger oligonucleotide B and extending the $A_1$ strand in the 5'-3' direction against B; or (ii) circularising $A_1$ through ligation of its 3' and 5' ends; or (iii) ligating the 5' end of $A_1$ to the 3' end of a ligation probe oligonucleotide C; in each case to create an oligonucleotide $A_2$;
d. priming $A_2$ with at least one single-stranded primer oligonucleotide and creating multiple copies of $A_2$, or a region of $A_2$; and
e. detecting a signal derived from the multiple copies and inferring therefrom the presence or absence of the polynucleotide target sequence in the analyte.

In embodiments of the invention wherein step (b) utilises a double strand-specific 5'-3' exonuclease, it is the 5' end of $A_0$ that is complementary to the target analyte and the common priming sequence and blocking group are located on the 3' side of the region complementary to the target. In a further embodiment, where molecular probes are to be used for detection in step (e), the probe oligonucleotide $A_0$ is configured to include an oligonucleotide identification region on the 3' side of the region complementary to the target sequence, and the molecular probes employed are designed to anneal to this identification region.

In embodiments of the invention wherein step (b) utilises a double strand-specific 5'-3' exonuclease, an exonuclease having 3' to 5' exonucleolytic activity can optionally be added to the reaction mixture, after step b. for the purpose of digesting any other nucleic acid molecules present whilst leaving $A_0$ and any material comprising partially digested strand $A_1$ intact. Suitably, this resistance to exonucleolysis is achieved as described previously.

It will be appreciated that the methods of the invention can be applied to a reaction mixture comprising a plurality of different analytes by using multiple different $A_0$ and optionally B, C or D components, each associated with a different molecular probe or the like. In such a multiplexed method, the detection of multiple target regions characteristic of a given cancer or a multiplicity of infectious diseases etc. is enabled. In one embodiment, it is in preferred that every different $A_2$ strand generated has a common primer site but different identification region, enabling one or a single set of primers to be used in amplification step (d).

In another aspect of the invention, there is provided the use of the methods described above to screen mammalian subjects, especially human patients, for the presence of infectious diseases, cancer or for the purpose of generating companion diagnostic information.

In a further aspect of the invention, there is provided control probes for use in the methods as described above. Embodiments of the current invention include those wherein the presence of a specific target sequence, or sequences, is elucidated by the generation of a fluorescent signal.

In such embodiments, there may inevitably be a level of signal generated from non-target DNA present in the sample. For a given sample, this background signal has a later onset than the 'true' signal, but this onset may vary between samples. Accurately detection of the presence of low concentrations of target sequence, or sequences, thus relies on knowledge of what signal is expected in its absence. For contrived samples references are available, but for true 'blind' samples from patients this is not the case. The control probes ($E_0$) are utilised to determine the expected background signal profile for each assay probe. The control probe targets a sequence not expected to be present in the sample and the signal generated from this probe can then be used to infer the expected rate of signal generation from the sample in the absence of target sequence.

Thus there is provided a method of detecting a target polynucleotide sequence in a given nucleic acid analyte characterised by the steps of:
a. adding a single-stranded probe oligonucleotide $A_0$ to a sample to anneal with a target analyte to create a first intermediate product which is at least partially double-stranded and in which the 3' end of $A_0$ forms a double-stranded complex with the analyte target sequence;
b. pyrophosphorolysing the first intermediate product with a pyrophosphorolysing enzyme in the 3'-5' direction from the 3' end of $A_0$ to create partially digested strand $A_1$ and the analyte;
c. (i) annealing $A_1$ to a single-stranded trigger oligonucleotide B and extending the $A_1$ strand in the 5'-3' direction against B; or (ii) circularising $A_1$ through ligation of its 3' and 5' ends; or (iii) ligating the 3' end of $A_1$ to the 5' end of a ligation probe oligonucleotide C; in each case to create an oligonucleotide $A_2$;
d. priming $A_2$ with at least one single-stranded primer oligonucleotide and creating multiple copies of $A_2$, or a region of $A_2$;
e. detecting a signal derived from the multiple copies;
f. either subsequently or concurrently repeating steps (a) to (e) using a second single-stranded probe oligonucleotide $E_0$ having a 3' end region at least partially mismatched to the target sequence, either using a separate aliquot of the sample or in the same aliquot and using a second detection channel;
g. inferring from the result of (f) the background signal expected to be generated from $A^0$ in the absence of any target analyte in the sample; and
h. through comparison of the expected background signal inferred in (g) with the actual signal observed in (e), inferring the presence of absence of the polynucleotide target sequence in the analyte.

In some embodiments, the method in step (e) according to the present invention occurs by:

i. labelling the multiple copies of $A_2$, or a region of $A_2$ using one or more oligonucleotide fluorescent binding dyes or molecular probes;

ii. measuring the fluorescent signal of the multiple copies produced in step (d);

iii. exposing the multiple copies to a set of denaturing conditions; and iv. detecting the presence of, and identifying, the amplified product by monitoring changes in the fluorescent signal of the multiple copies during exposure to the denaturing conditions, in comparison with the same measurement performed on the product of step (f).

In one embodiment, the control probe ($E_0$) and $A_0$ are added to separate portions of the sample while in another embodiment the $E_0$ and $A_0$ are added to the same portion of the sample and different detection channels (e.g. different colour dyes) used to measure their respective signals. The signal generated by $E_0$ may then be utilised to infer and correct for the background signal expected to be generated by $A_0$ in the absence of the polynucleotide target sequence in the sample. For example, a correction of the background signal may involve the subtraction of the signal observed from $E_0$ from that observed from $A_0$, or through the calibration of the signal observed from $A_0$ using a calibration curve of the relative signals generated by $A_0$ and $E_0$ under varying conditions.

In one embodiment, a single $E_0$ can be used to calibrate all of the assay probes which may be produced.

In one embodiment, a separate $E_0$ may be used to calibrate each amplicon of the sample DNA generated in an initial amplification step. Each amplicon may contain multiple mutations/target sequences of interest, but a single $E_0$ will be sufficient to calibrate all of the assay probes against a single amplicon.

In a further embodiment, a separate $E_0$ may be used for each target sequence. For example, if a C>T mutation is being targeted, an $E_0$ could be designed that targets a C>G mutation in the same site that is not known to occur in patients. The signal profile generated by $E_0$ under various conditions can be assessed in calibration reactions and these data used to infer the signal expected from the assay probe targeting the C>T variant when this variant is not present.

Figure 9:
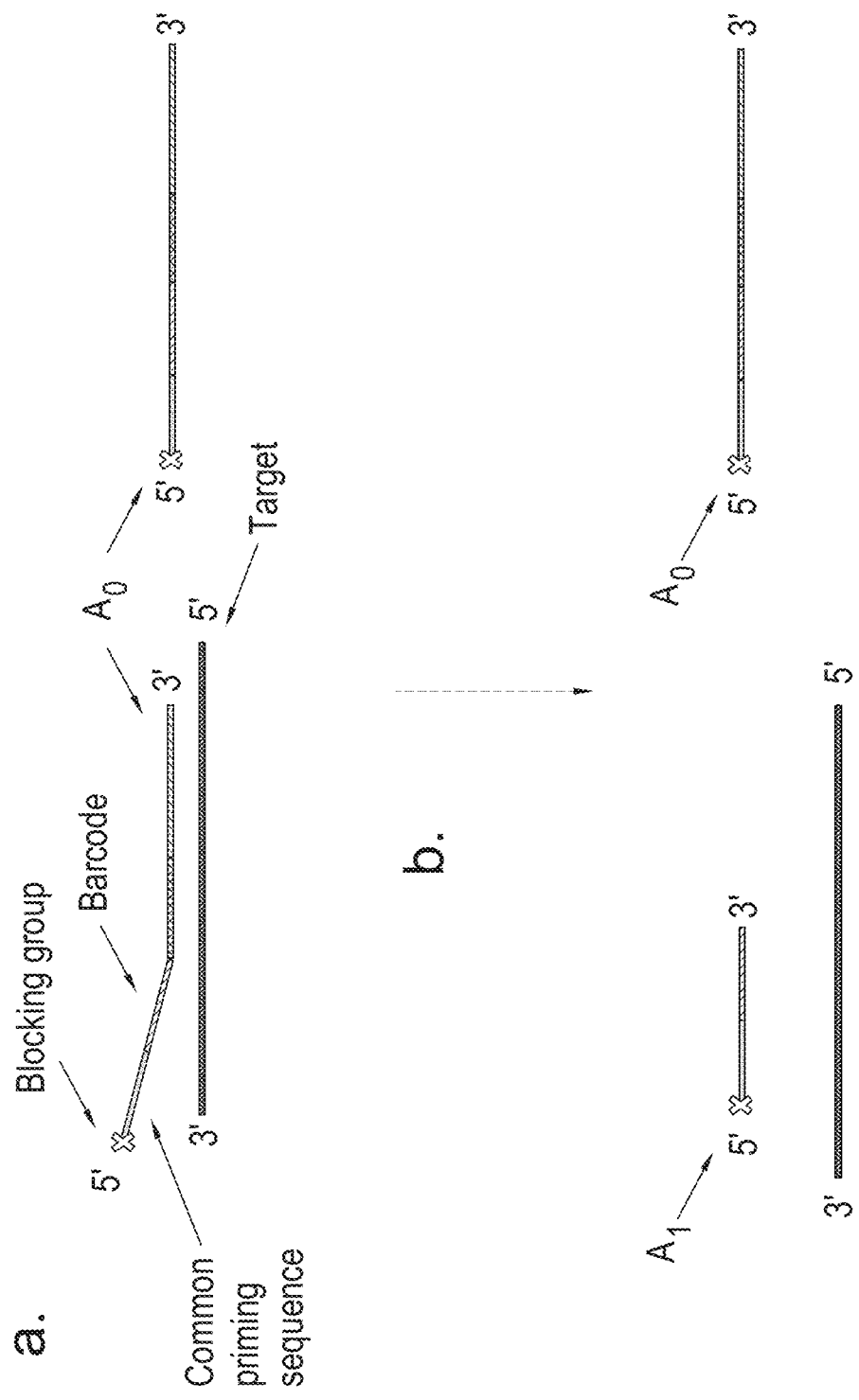
FIG. 9: One embodiment of steps a to b of the method of the invention. In step a, a single-stranded probe oligonucleotide $A_0$ anneals to a target polynucleotide sequence to create a first intermediate product which is at least partially double-stranded and in which the 3' end of $A_0$ forms a double-stranded complex with the target polynucleotide sequence. In this simplified embodiment of the invention there are two molecules of $A_0$ present and one target polynucleotide sequence, in order to illustrate how $A_0$ that has not annealed to a target does not take part in further steps of the method. In this illustrative example of step a, the 3' end of $A_0$ anneals to the target polynucleotide sequence whilst the 5' end of $A_0$ does not. The 5' end of $A_0$ comprises a 5' chemical blocking group, a common priming sequence and a barcode region.

One embodiment of the method of the invention can be seen in FIGS. 9 to 12. In FIG. 9, one embodiment of steps a to b is illustrated. In step a, a single-stranded probe oligonucleotide $A_0$ anneals to a target polynucleotide sequence to create a first intermediate product which is at least partially double-stranded and in which the 3' end of $A_0$ forms a double-stranded complex with the target polynucleotide sequence. In this simplified embodiment of the invention there are two molecules of $A_0$ present and one target polynucleotide sequence, in order to illustrate how $A_0$ that has not annealed to a target does not take part in further steps of the method. In this illustrative example of step a, the 3' end of $A_0$ anneals to the target polynucleotide sequence whilst the 5' end of $A_0$ does not. The 5' end of $A_0$ comprises a 5' chemical blocking group, a common priming sequence and a barcode region.

In step b, the partially double-stranded first intermediate product is pyrophosphorylsed with a pyrophosphorolysing enzyme in the 3'-5' direction from the 3' end of $A_0$ to create a partially digested strand $A_1$, the analyte and the undigested $A_0$ molecule which did not anneal to a target in step a.

In FIG. 10, one embodiment of steps c(i) to d is illustrated. In step c(i), $A_1$ is annealed to a single-stranded trigger oligonucleotide B and the $A_1$ strand is extended in the 5'-3' direction against B to create an oligonucleotide $A_2$. In this illustrative example, trigger oligonucleotide B has a 5' chemical block. The undigested $A_0$ from step b of the method anneals to the trigger oligonucleotide B, however it is unable to be extended in the 5'-3' direction against B to generate sequences that are the target for the amplification primers of step d.

In step d, $A_2$ is primed with at least one single-stranded primer oligonucleotide and multiple copies of $A_2$, or a region of $A_2$ are created.

In FIG. 11, one embodiment of steps c(ii) to d is illustrated. In step c(ii), $A_1$ is annealed to a splint oligonucleotide D, and then circularised by ligation of its 3' and 5' ends. In step d, the now circularised $A_2$ is primed with at least one single-stranded primer oligonucleotide and multiple copies of $A_2$, or a region of $A_2$ are created. In this illustrative example, the splint oligonucleotide D is unable to extend against $A_1$ by virtue of either a 3'-modification (chemical in this illustration) or through a nucleotide mismatch between the 3' end of D and the corresponding region of $A_2$.

In step d, $A_2$ is primed with at least one single-stranded primer oligonucleotide and multiple copies of $A_2$, or a region of $A_2$ are created.

In FIG. 12, one embodiment of steps c(iii) to d is illustrated. In step c(ii), $A_1$ is annealed to a splint oligonucleotide D, and then circularised by ligation of its 3' and 5' ends. In step d, the now circularised $A_2$ is primed with at least one single-stranded primer oligonucleotide and multiple copies of $A_2$, or a region of $A_2$ are created. In this illustrative example, the splint oligonucleotide D is unable to extend against $A_1$ by virtue of either a 3'-modification (chemical in this illustration) or through a nucleotide mismatch between the 3' end of D and the corresponding region of $A_2$.

In step d, $A_2$ is primed with at least one single-stranded primer oligonucleotide and multiple copies of $A_2$, or a region of $A_2$ are created.

The specificity of the methods of the current invention may be improved by blocking at least a portion of wild-type DNA, promoting annealing of $A_0$ only to the target polynucleotide sequences. Blocking oligonucleotides can be used to improve the specificity of the polymerase chain reaction (PCR). The general technique used is to design an oligonucleotide that anneals between the PCR primers and is not able to be displaced or digested by the PCR polymerase. The oligonucleotide is designed to anneal to the non-target (usually healthy) sequence, while being mismatched (often by a single base) to the target (mutant) sequence. This mismatch results in a different melting temperature against the two sequences, the oligonucleotide being designed to remain annealed to the non-target sequence at the PCR extension temperature while dissociating from the target sequence.

The blocking oligonucleotides may often have modifications to prevent its digestion by the exonuclease activity of the PCR polymerase, or to enhance the melting temperature differential between the target and non-target sequence.

The incorporation of a locked nucleic acid (LNA) or other melting temperature altering modification into a blocking oligonucleotide can significantly increase the differential in melting temperature of the oligonucleotide against target and non-target sequences.

Thus there is provided an embodiment of the invention wherein blocking oligonucleotides are used. The blocking oligonucleotides must be resistant to the pyrophosphorolysing (PPL) reaction to ensure they are not digested or displaced. This can be achieved in a number of different ways, for example via mismatches at their 3' ends or through modifications such as phosphorothioate bonds or spacers.

In such embodiments or an aspect of the present invention where blocking oligonucleotides are used, the method of detecting a target polynucleotide sequence in a given nucleic acid analyte is characterised by the steps of:
a. annealing single-stranded blocking oligonucleotides to at least a subset of non-target polynucleotide sequences;
b. annealing the analyte target sequence to a single-stranded probe oligonucleotide $A_0$ to create a first intermediate product which is at least partially double-stranded and in which the 3' end of $A_0$ forms a double-stranded complex with the analyte target sequence;
c. pyrophosphorolysing the first intermediate product with a pyrophosphorolysing enzyme in the 3'-5' direction from the 3' end of $A_0$ to create partially digested strand $A_1$ and the analyte;
d. (i) annealing $A_1$ to a single-stranded trigger oligonucleotide B and extending the $A_1$ strand in the 5'-3' direction against B; or (ii) circularising $A_1$ through ligation of its 3' and 5' ends; or (iii) ligating the 3' end of $A_1$ to the 5' end of a ligation probe oligonucleotide C; in each case to create an oligonucleotide $A_2$;
e. priming $A_2$ with at least one single-stranded primer oligonucleotide and creating multiple copies of $A_2$, or a region of $A_2$; and
f. detecting a signal derived from the multiple copies and inferring therefrom the presence or absence of the polynucleotide target sequence in the analyte.

In one embodiment, the blocking oligonucleotides are made to be resistant to the pyrophosphorolysing reaction via mismatches at their 3' ends. In another embodiment, the blocking oligonucleotides are made to be resistant via the presence of a 3'-blocking group. In another embodiment the blocking oligonucleotides are made to be resistant via the presence of spacers or other internal modifications. In a further embodiment the blocking oligonucleotides include both a melting temperature increasing modification or modified nucleotide base and are rendered resistant to pyrophosphorolysis.

The invention is now illustrated with reference to the following experimental data.

Example 1: Pyrophosphorolysis Specificity Against Single Nucleotide Mismatches

A single-stranded first oligonucleotide 1 (SEQ ID NO 1) was prepared, having the following nucleotide sequence:

5'-CGCTCGATGTATACGCTCGGACCACTCGTACCTCGAACTGTCGTTAG
TATTTTTATATGTAGTTTCTGAAGTAGATATGGCAGCACATAATGAC-3' wherein A, C, G, and T represent nucleotides bearing the relevant characteristic nucleobase of DNA.

A set of single-stranded oligonucleotides 2-6 (SEQ ID NOs 2-6) was also prepared, having the following nucleotide sequences in the 5' to 3' direction:

2:
AGTACAAATATGTCATTATGTGCTGCCATATCTACTTCAGAAACTACATA

TAAAAATACTAACTTTAAGG

3:
AGTACAAATATCTCATTATGTGCTGCCATATCTACTTCAGAAACTACATA

TAAAAATACTAACTTTAAGG

4:
AGTACAAATATGTCATTATGAGCTGCCATATCTACTTCAGAAACTACATA

TAAAAATACTAACTTTAAGG

5:
AGTACAAATATGTCATTATGTGCTGCCATAACTACTTCAGAAACTACATA

TAAAAATACTAACTTTAAGG

6:
AGTACAAATATGTCATTATGTGCTGCCATATCTACTTCAGTAACTACATA

TAAAAATACTAACTTTAAGG wherein oligonucleotide 2 includes a 52 base region complementary to the 52 bases at the 3' end of oligonucleotide 1 and oligonucleotides 3-6 include the same region with single nucleotide mismatches at positions 1, 10, 20 and 30 respectively.

A reaction mixture was then prepared, having a composition corresponding to that derived from the following formulation:

20 uL 5× buffer pH 8.0

10 uL oligonucleotide 1, 3000 nM 10 uL oligonucleotide 2, 3, 4, 5 or 6, 3000 nM 2.5 U Mako DNA polymerase (ex. Qiagen Beverly)

10 uL inorganic pyrophosphate, 6 mM 0.04 U Apyrase

Water to 100 uL wherein the 5× buffer comprised the following mixture:

50 uL Trizma Acetate, 1M, pH 8.0

25 uL aqueous Magnesium Acetate, 1M 25 uL aqueous Potassium Acetate, 5M 50 uL Triton X-100 surfactant (10%)

Water to 1 mL

Pyrophosphorolysis of oligonucleotide 1 was then carried out by incubating the mixture at 37° C. for 120 minutes and the resulting reaction product analysed by gel electrophoresis.

Figure 1:
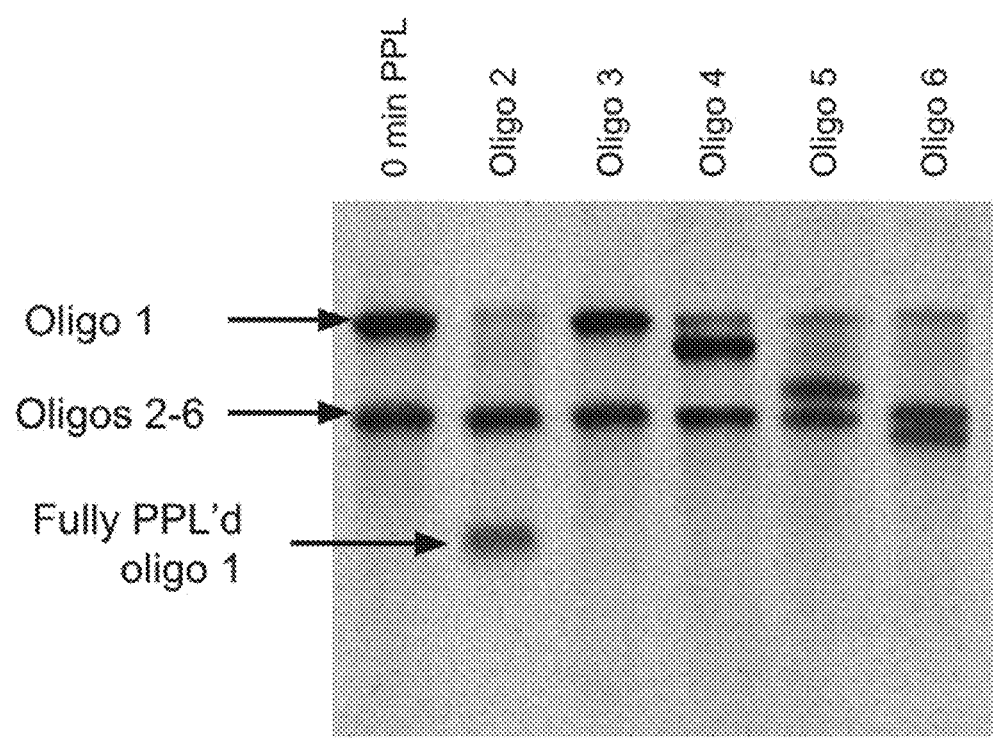
FIG. 1: Gel electrophoresis image of the reaction products of Example 1. It can be seen that in the presence of oligonucleotide 2, oligonucleotide 1 is degraded to the length at which it melts from oligonucleotide 2, leaving a shortened oligonucleotide approximately 50 nucleotides in length. Conversely, in the presence of oligonucleotide 3, no pyrophosphorolysis is observed due to the single nucleotide mismatch at the 3' end of oligonucleotide 1. In the presence of oligonucleotides 4-6, pyrophosphorolysis of oligonucleotide 1 proceeds to the position of the single base mismatch at which point it stops, leaving a shortened oligonucleotide which is not further degraded.

The results of this analysis are shown in FIG. 1, where it can be seen that in the presence of oligonucleotide 2, oligonucleotide 1 is degraded to the length at which it melts from oligonucleotide 2, leaving a shortened oligonucleotide approximately 50 nucleotides in length. Conversely, in the presence of oligonucleotide 3, no pyrophosphorolysis is observed due to the single nucleotide mismatch at the 3' end of oligonucleotide 1. In the presence of oligonucleotides 4-6, pyrophosphorolysis of oligonucleotide 1 proceeds to the position of the single base mismatch at which point it stops, leaving a shortened oligonucleotide which is not further degraded.

Example 2: Circularisation of Degraded Probe and Exonucleolytic Digestion of Uncircularised DNA Single-stranded first oligonucleotides 1 (SEQ ID NO 7) and 2 (SEQ ID NO 8) were prepared, having the following nucleotide sequences:

1:
5'-PCGCTCGATGTATACGCTCGGACCACTCGTACCTCGAACTGTCGTTA

GTATTTTTATATGTAGTTTCTGAAGTAGATATGGCAGCACATAAT

GAC-3'

2:
5'-PATGTTCGATGAGGCACGATATAGATGTACGCTTTGACATACGCTTT

GACAATACTTGAGCAGTCGGCAGATATAGGATGTTGCAAGCTCCGTGAGT

CCCACAAACCAATAACCTCGTTTTTTATATGTAGTT-3' wherein A, C, G, and T represent nucleotides bearing the relevant characteristic nucleobase of DNA and P represents a 5' phosphate group, and wherein oligonucleotide 1 comprises a shortened oligonucleotide 2 as would be obtained through pyrophosphorolysis of oligonucleotide 2 against a suitable target oligonucleotide.

A third single-stranded oligonucleotide 3 (SEQ ID NO 9) was also prepared, having the following nucleotide sequence:

TATCGTGCCTCATCGAACATAACTACATATAAAAAACGAGGTTATTGGTT

TGTGGC/3ddC/ wherein /3 ddC/ represents a 3' dideoxycytosine nucleotide, and wherein oligonucleotide 3 has a 5' end complementary to the 3' end of oligonucleotide 1 and an internal region of oligonucleotide 2, and a 3' end complementary to the 5' ends of oligonucleotides 1 and 2.

A reaction mixture was then prepared, having a composition corresponding to that derived from the following formulation:
  20 uL 5× buffer pH 8.0
  10 uL oligonucleotide 1 or 2, 3000 nM
  10 uL oligonucleotide 3, 3000 nM
  7 U E. Coli Ligase
  Water to 100 uL
wherein the 5× buffer comprised the following mixture:
  50 uL Trizma Acetate, 1M, pH 8.0
  25 uL aqueous Magnesium Acetate, 1M
  25 uL aqueous Potassium Acetate, 5M
  50 uL Triton X-100 surfactant (10%)
  Water to 1 mL
Oligonucleotide ligation was then carried out by incubating the mixture at 37° C. for 30 minutes.

A second reaction mixture was then prepared, having a composition corresponding to that derived from the following formulation:
  20 uL 5× buffer pH 8.0
  125 U Exonuclease III or equivalent volume water
  Water to 100 uL
wherein the 5× buffer comprised the following mixture:
  50 uL Trizma Acetate, 1M, pH 8.0
  25 uL aqueous Magnesium Acetate, 1M
  25 uL aqueous Potassium Acetate, 5M
  50 uL Triton X-100 surfactant (10%)
  Water to 1 mL The first and second reaction mixes were then combined, and the resulting mix incubated at 37° C. for 30 minutes to allow exonucleolytic digestion of any uncircularised DNA. The resulting solution was then analysed by gel electrophoresis.

Figure 2:
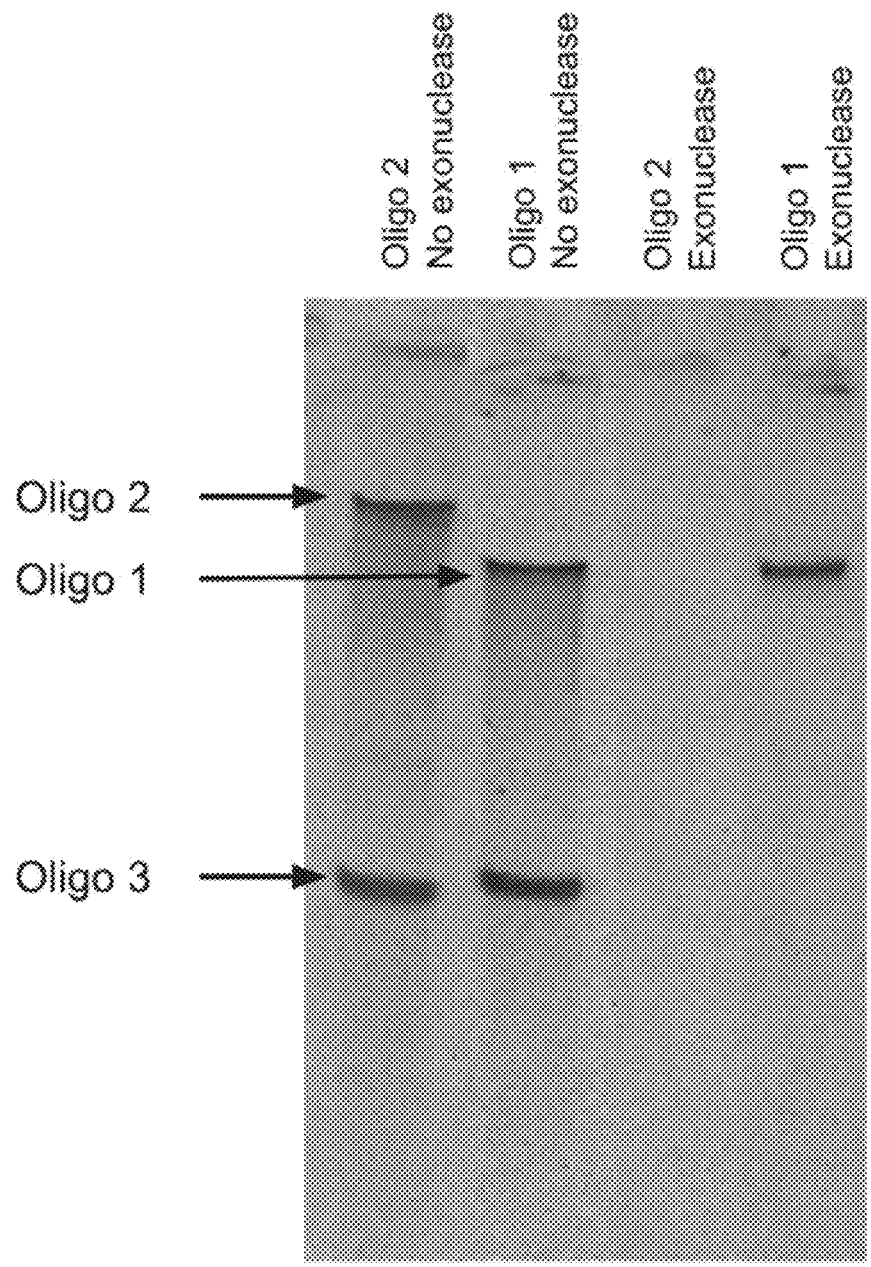
FIG. 2: Gel electrophoresis image of the reaction products of Example 2. It can be seen that the shortened oligonucleotide (oligonucleotide 1) is efficiently circularised by the ligation reaction and survives subsequent exonuclease digestion, while the un-shortened oligonucleotide (oligonucleotide 2) is not circularised and is efficiently digested.

The results of this analysis are shown in FIG. 2 where it can be seen that the shortened oligonucleotide (oligonucleotide 1) is efficiently circularised by the ligation reaction and survives the subsequent exonuclease digestion, while the un-shortened oligonucleotide (oligonucleotide 2) is not circularised and is efficiently digested.

Example 3: Amplification of Circularised Probe

A pair of single stranded oligonucleotide primers 1 (SEQ ID NO 10) and 2 (SEQ ID NO 11) were prepared, having the following nucleotide sequences:

1:
TGCTCAAGTATTGTCAAAGC

2:
CGGCAGATATAGGATGTTGC wherein A, C, G, and T represent nucleotides bearing the relevant characteristic nucleobase of DNA.

A reaction mixture was then prepared, having a composition corresponding to that derived from the following formulation:
  20 uL 5× Phusion Flex HF reaction buffer
  0.1 uL final reaction mix from Example 2
  Water to 100 uL
A second reaction mixture was also prepared, having a composition corresponding to that derived from the following formulation:
  20 uL 5× Phusion Flex HF reaction buffer
  10 uL betaine, 2.5M
  10 uL oligonucleotide 1, 3000 nM
  10 uL oligonucleotide 2, 3000 nM
  10 uL dNTPs, 2 mM
  2 U Phusion Hot Start Flex DNA polymerase
  Water to 100 uL
The second reaction mix was then combined with 0.1 uL of the first reaction mix, and the resulting mixture incubated at 98° C. for 1 minute followed by 30 cycles of (98° C.×20 sec; 55° C.×30 sec; 68° C.×30 sec) to allow exponential amplification to take place via the polymerase chain reaction.

Figure 3:
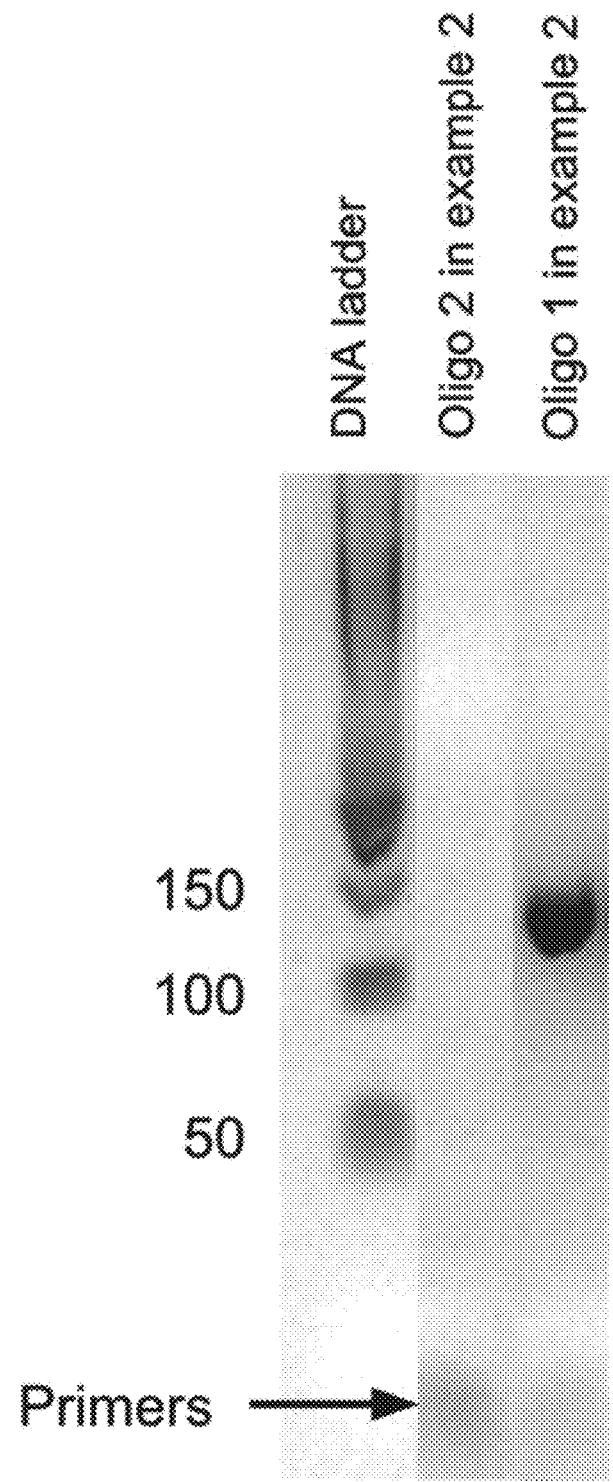
FIG. 3: Gel electrophoresis image of the reactions products of Example 3. It can be seen that when the shortened oligonucleotide was present, and circularised, in Example 2 a large amount of product is produced by this amplification. Conversely, when the un-shortened oligonucleotide was present in Example 2, and no circularisation took place, there was no observable amplification of DNA.

The resulting reaction product was then analysed by gel electrophoresis, the results of which are shown in FIG. 3. From this analysis it can be seen that when the shortened oligonucleotide was present in Example 2 and was circularised, a large amount of product is produced by this amplification. Conversely, when the un-shortened oligonucleotide was present in Example 2 and no circularisation took place there was no observable amplification of DNA.

Example 4: Pyrophosphorolysis Using Pyrophosphate Analogues

A single-stranded first oligonucleotide 1 (SEQ ID NO 12) was prepared, having the following nucleotide sequence:

5'-ATGACCTCGTAAGCCAGTGTCAGAGFFTTQTTCCAGCCGT-3' wherein A, C, G, and T represent nucleotides bearing the relevant characteristic nucleobase of DNA; F represents a deoxythymidine nucleotide (T) labelled with Atto 594 dye using conventional amine-attachment chemistry and Q represents a deoxythymidine nucleotide labelled with a BHQ-2 quencher.

Another single-stranded oligonucleotide 2 (SEQ ID NO 13) was also prepared, having the following nucleotide sequence:

5'-TTCACACGGCTGGAAAAAAACTCTGACACTGGCTTACGAGGTCATTA

GATX-3' wherein X represents an inverted 3' dT nucleotide, such that when oligonucleotide 2 is annealed to oligonucleotide 1 the 3' end of oligonucleotide 1 is recessed, making it a target for pyrophosphorolysis, while the 3' end of oligonucleotide 2 is protected from pyrophosphorolysis by the presence of the terminal inverted nucleotide.

A reaction mixture was then prepared, having a composition corresponding to that derived from the following formulation:
  20 uL 5× buffer pH 8.0
  10 uL oligonucleotide 1, 1000 nM
  10 uL oligonucleotide 2, 1000 nM
  2.5 U Mako DNA polymerase (ex. Qiagen Beverly)
  10 uL inorganic pyrophosphate, 6 mM OR imidodiphosphate, 10 mM OR water
  Water to 100 uL
wherein the 5× buffer comprised the following mixture:
  50 uL Trizma Acetate, 1M, pH 8.0
  25 uL aqueous Magnesium Acetate, 1M
  25 uL aqueous Potassium Acetate, 5M
  50 uL Triton X-100 surfactant (10%)
  Water to 1 mL Pyrophosphorolysis of oligonucleotide 1 was then carried out by incubating the mixture at 37° C. for 75 minutes. As oligonucleotide 1 was progressively pyrophosphorolysed, the fluorescent dye molecules were separated from the quenchers and were then able to generate a fluorescent signal. The growth in this fluorescence during the incubation was monitored using a CLARIOStar microplate reader (ex. BMG Labtech) and used to infer the rate of pyrophosphorolysis of the oligonucleotide in the presence of inorganic pyrophosphate, imidodiphosphate or water.

Figure 4:
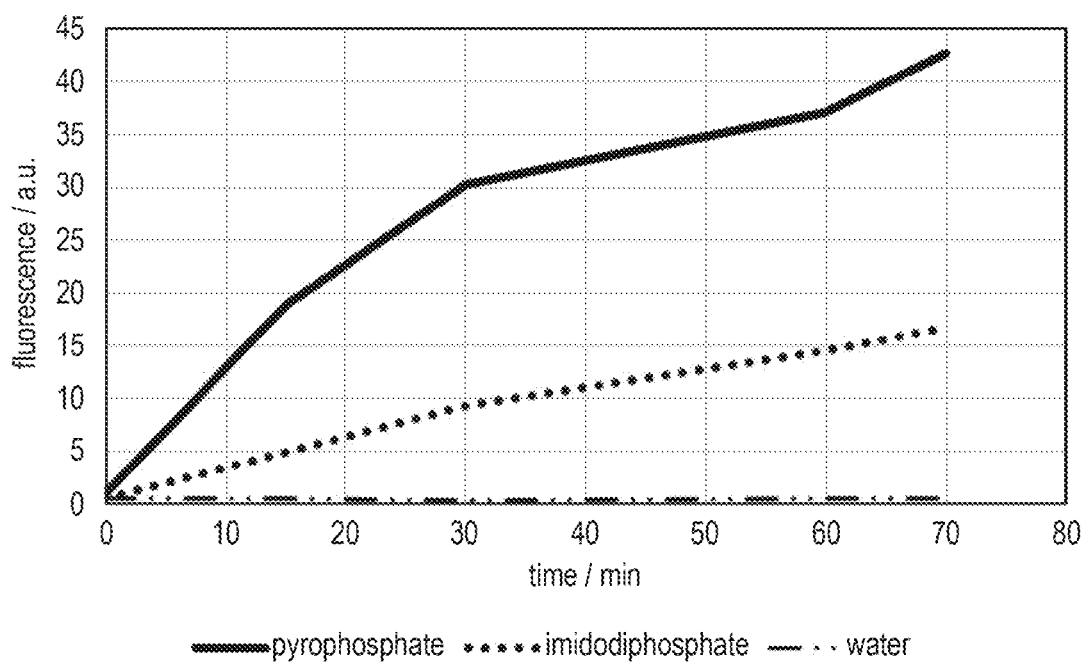
FIG. 4: Fluorescence traces measured as described in Example 4. It can be seen that pyrophosphorolysis proceeds in the presence of pyrophosphate or imidodiphosphate, but not in their absence. Similarly, in a comparative experiment where no polymerase was present no fluorescent signal was generated. Pyrophosphorolysis in the presence of pyrophosphate produces free nucleotide triphosphates, while pyrophosphorolysis in the presence of imidodiphosphate produces modified free nucleotide triphosphates with an N—H group in place of 0 between the beta and gamma phosphates (2'-Deoxynucleoside-5'-l(($\beta,\gamma$)-imidoltriphosphates)

The results of this experiment are shown graphically in FIG. 4. From this it can be seen that pyrophosphorolysis proceeds in the presence of pyrophosphate or imidodiphosphate, but not in their absence. Similarly, in a comparative experiment where no polymerase was present no fluorescent signal was generated. Pyrophosphorolysis in the presence of pyrophosphate produces free nucleotide triphosphates, while pyrophosphorolysis in the presence of imidodiphosphate produces modified free nucleotide triphosphates with an N—H group in place of 0 between the beta and gamma phosphates (2'-Deoxynucleoside-5'-[(β,γ)-imido]triphosphates).

Example 5: Melting Curve Analysis

The methods of the current invention were performed to detect the presence of, and identify, three different mutations which can occur in the human EGFR gene: T790M (exon 20), C797S_(exon 20) and L861Q (exon 21).

Six samples containing wild-type genomic DNA were prepared. Three of these samples were spiked with a single synthetic mutant sequence for each of the three mutations of interest such that the final mutant allele fraction in these samples was 1%. To each sample was added a probe oligo $A_0$ designed for the detection of a different single mutation:

T790M (SEQ ID NO 14):
5'-PATGTTCGATGAGCTTTGACAATACTTGAGCACGGCAGATATAGGAT

GTTGCGAAGGGCATGAGCTGCATGATGAGCTG-3'

C7975 (SEQ ID NO 15):
5'-PATGTTCGATGAGCTTTGACAATACTTGAAGCTCGCAGATATAGGAT

GTTGCGATAGTCCAGGAGGCTGC-3'

L861Q (SEQ ID NO 16):
5'-PATGTTCGATGAGCTTTGACAATACTTGATCGATGCAGATATAGGAT

GTTGCGATCCGCACCCAGCTGTTTGGC-3'

The samples were subjected to pyrophosphorolysis through addition of inorganic pyrophosphate ion and Mako DNA polymerase and incubation at 41° C. Following pyrophosphorolysis of the probe oligos, ligation was performed through addition of E. Coli Ligase and splint oligos with the following sequences:

T790M (SEQ ID NO 17):
    5'-TGTCAAAGCTCATCGAACATGCCCTTCGCAACATCT-3'

C7975 (SEQ ID NO 18):
    5'-TGTCAAAGCTCATCGAACATTCCTGGACTATCGCAT-3'

L861Q (SEQ ID NO 19):
    5'-AGCTCATCGAACATCTGGGTGCGGATCGCAACAA-3'

Following ligation, the samples were subjected to hyperbranched rolling circle amplification through addition of dNTPs, BstLF DNA polymerase, Sybr Green intercalating dye, a mutation-specific forward primer and a universal reverse primer having the sequences below, followed by incubation at 60° C. for 70 minutes.

T790M (SEQ ID NO 20):
    5'-ACATCCTATATCTGCCGT-3'

C7975 (SEQ ID NO 21):
    5'-CATCGAACATTCCTGGACTA-3'

L861Q (SEQ ID NO 22):
    5'-TCATCGAACATCTGGGTGCG-3'

Universal reverse primer (SEQ ID NO 23):
    5'-ATGTTCGATGAGCTTTGACA-3'

Figure 5:
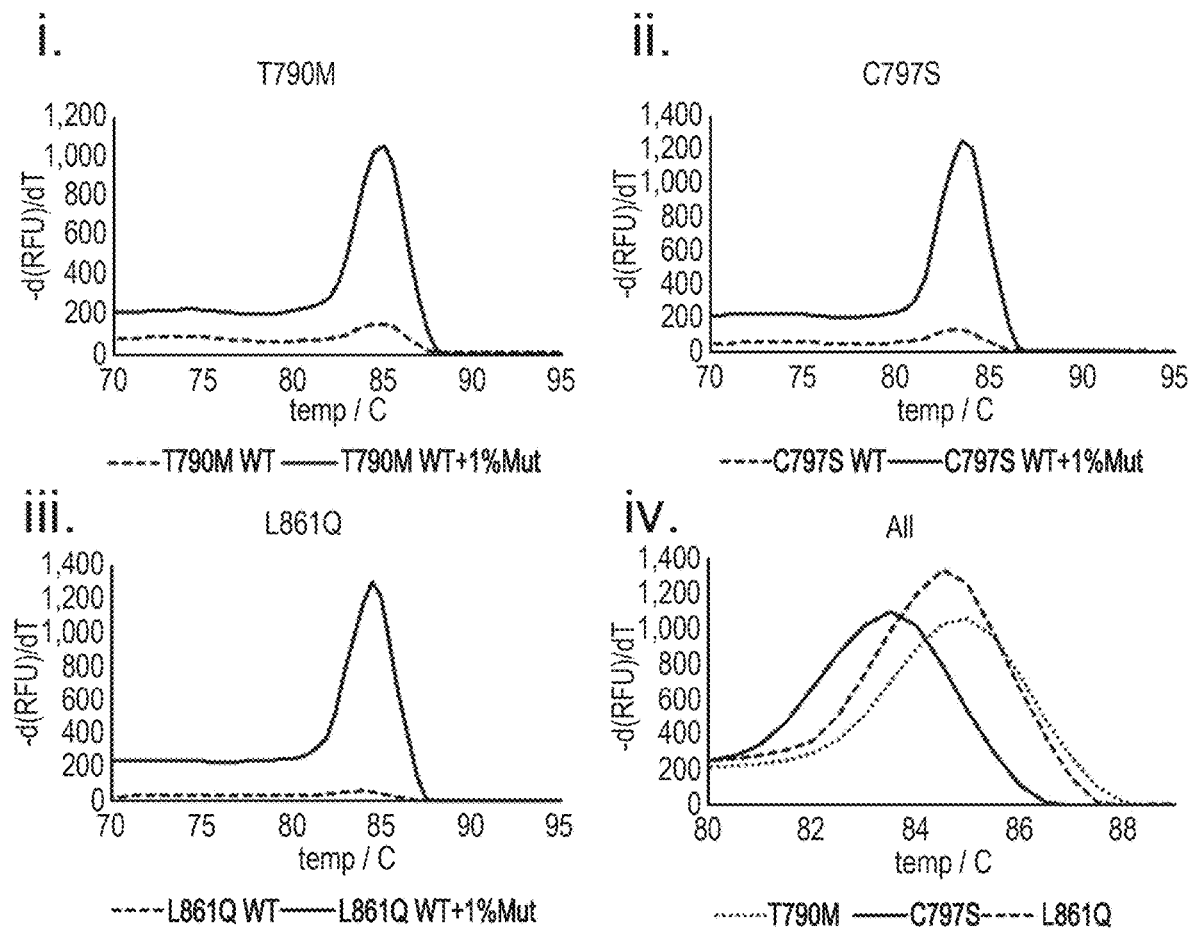
FIG. 5: Melt peak results for amplification products produced from a rolling circle amplification, Example 5, using primers for three different mutations which can occur to the EGFR gene: (i) T790M (exon 20), (ii) C797S (exon 20) and (iii) L861Q (exon 21). The temperature was raised to 95° C., with measurements taken at 0.5° C. intervals. In (iv), the position of the melting peak can be used to identify which mutation i.e. T790M, C797S or L861Q is present.

The temperature of the samples was then increased from 70° C. to 95° C. and a fluorescence measurement taken at every 0.5° C. The resulting data curves were differentiated to produce melting peaks, the results of which are shown in FIG. 5. It can be seen that the presence of a significant melting peak can thus be used to infer the presence of the mutation targeted by a given probe, while the position of this peak can be used to identify the nature of the mutation.

Example 6: Applications and Uses

The following applications described below provide some examples of how the methods of the present invention can be applied.

Companion Diagnostics

The methods of the present invention can be used to detect specific genetic markers in a sample which may be used to help guide the selection of appropriate therapy. These markers may be tumour-specific mutations, or may be wild-type genomic sequences, and may be detected using tissue, blood or any other patient sample type.

Resistance Monitoring

Repeated testing of patient samples during treatment of disease may allow early detection of developed resistance to therapy. As an example of this application is in non-small cell lung carcinoma (NSCLC), in which epidermal growth factor receptor (EGFR) inhibitors (e.g. gefitinib, erlotinib) are commonly used as first line treatments. During treatment the tumour can often develop mutations in the EGFR gene (e.g. T790M, C797S) which confer resistance to the drug. Early detection of these mutations may allow for transfer of the patient onto alternative therapies (e.g. Tagrisso).

Typically patients being monitored for resistance onset can be too sick for repeated tissue biopsy to be carried out. Repeated tissue biopsy may also be expensive, invasive and carries associated risks. It is preferable to test from blood, but there may be very low copy numbers of the mutations of interest in a reasonable blood drawn sample. Monitoring therefore requires sensitive testing from blood samples using a method of the present invention in which the method is simple and cost effective to carry out such that it can be regularly performed.

Recurrence Monitoring

In this application example, patients who have been declared free of disease following treatment may be monitored over time to detect the recurrence of disease. This needs to be done non-invasively and requires sensitive detection of target sequences from blood samples. By using the method of the present invention, it provides a simple and low-cost method that can be regularly performed. The sequences targeted may be generic mutations known to be common in the disease of interest, or can be custom panels of targets designed for a specific patient based on detection of variants in the tumour tissue prior to remission.

Minimal Residual Disease (MRD) Monitoring

For some cancers there are residual cancer cells that remain in a patient after treatment, it is a major cause of relapse in cancer and leukaemia. MRD monitoring and testing has several important roles: determining whether treatment has eradicated the cancer or whether traces remain, comparing the efficacy of different treatments, monitoring patient remission status as well as detecting recurrence of leukaemia, and choosing the treatment that will best meet those needs.

Screening

Population screening for early detection of disease has been a long-held goal, particularly in cancer diagnostics. The challenge is two-fold: the identification of panels of markers which allow confident detection of disease without too many false negatives, and the development of a method with sufficient sensitivity and low enough cost. The methods of the present invention could be used to address larger panels of mutations than PCR-based tests but with a much simpler workflow and lower cost than sequencing-based diagnostics.

Organ Transplant Rejection

When a transplanted organ is rejected by the recipient, the DNA from this organ is shed into the recipient's bloodstream. Early detection of this DNA would allow early detection of rejection. This could be achieved using custom panels of donor-specific markers, or by using panels of variants known to be common in the population, some of which will be present in the donor and some in the recipient. Routine monitoring of organ recipients over time could be enabled by the low cost and simple workflow of the present invention disclosed herein.

Non-Invasive Prenatal Testing (NIPT)

It has long been known that fetal DNA is present in maternal blood, and the NIPT market is now quite saturated with companies using sequencing the identify mutations and count copy numbers of specific chromosomes to enable detection of fetal abnormalities. The methods of the present invention as disclosed herein have the ability to detect mutations at very low allele fractions, potentially allowing earlier detection of fetal DNA. Identification of common mutations in a given population would allow assays to be developed that target mutations that may be present in either the maternal or fetal DNA or to allow detection of abnormalities at an earlier stage of pregnancy.

Example 7: Single Well Multiplexing Techniques

In some instances, there are groups of mutations or target sequences for which the presence but not the identity of any one of the targets should be identified. In others, information is required on both the presence and the identity of the mutation or sequences. In both instances, it is beneficial to multiplex the reaction such that multiple targets are assayed in a single reaction volume. This leads to improved efficiency of the process, increasing either the number of samples that can be processed at one time or the size of the panel of targets that can be assayed. When the presence but not the identity of a target sequence is required, multiplexing can be as simple as combining the probes for multiple targets into a single reaction volume. One key advantage of the methods of the current invention over standard PCR is that one single set of primers can be used to amplify all of the 'activated' probes ($A_2$) in the final step of the reaction.

Using Exon19 deletions on the EGFR gene, the inventors have demonstrated 10-fold multiplexed detection at 0.1% mutant allele frequency (MAF) in a single reaction.

Figure 6:
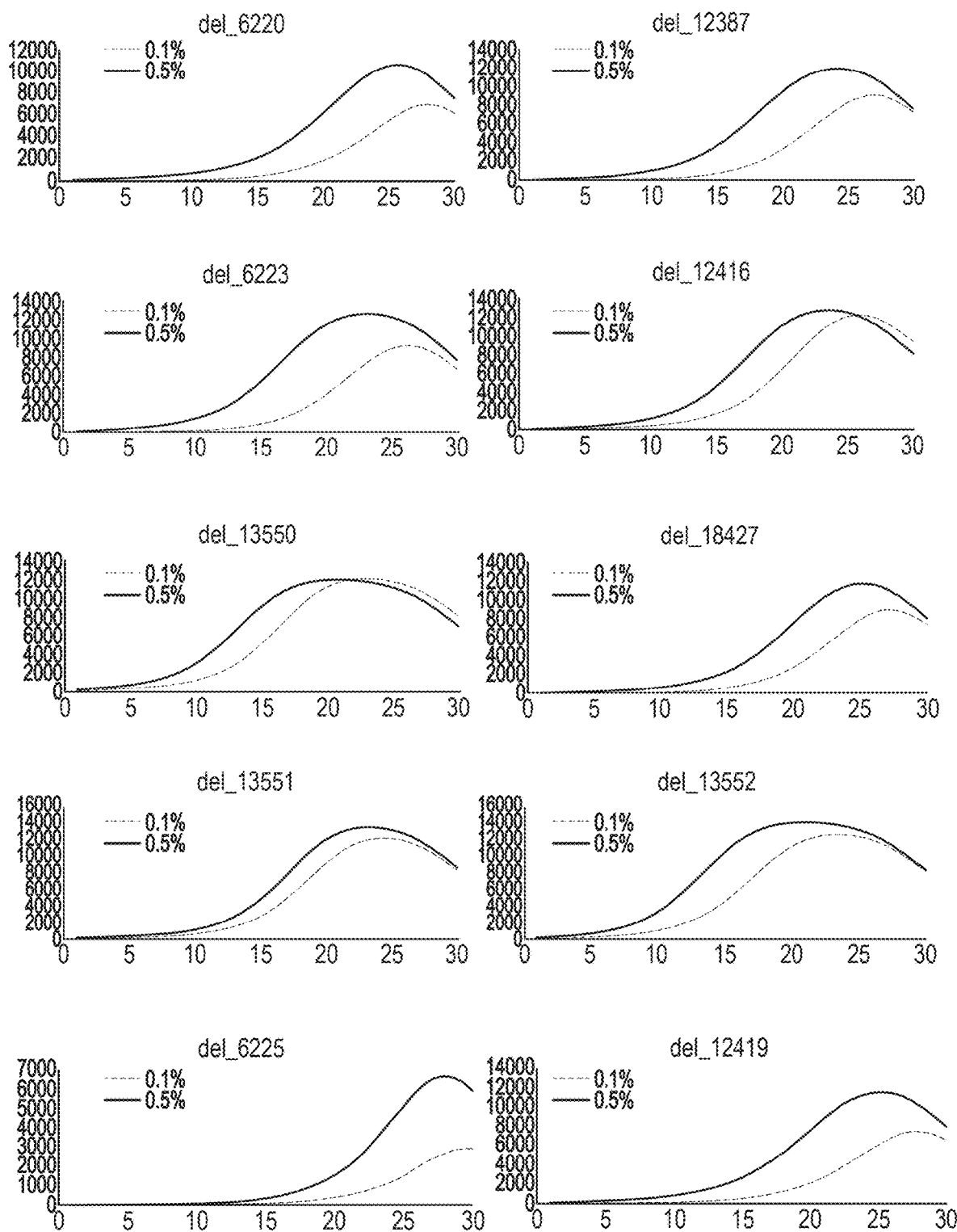
FIG. 6: Signal over wild-type (WT) results for single-well 10-plex detection of epidermal growth factor receptor (EGFR) Exon19 mutations at 0.1% and 0.5% mutant allele frequency (MAF) as described in Example 7.

20 samples were prepared, each comprising wildtype (WT) DNA spiked with 0.1% or 0.5% of one of 10 different Exon19 deletions. An addition sample comprising only WT DNA was used as a control. Probes for the detection of all 10 different Exon19 mutations were added to every sample and the reaction performed using standard conditions. The results (see FIG. 6) show clear detection of each mutation at both 0.5% and 0.1% MAF.

Detection can be performed using standard techniques—intercalating dye, labelled probes (Taqman, Scorpion, stem-loop primers), molecular beacons or any of the other standard techniques which will be known to the person skilled in the art.

When the identity of the target is required it is most likely that a multi-colour system is used to identify which probe has been activated ($A_2$). This naturally necessitates a probe design in which there are different 'barcode' sequences in the probes for different targets, which are then used for identification. Identification can then be performed as discussed previously.

Figure 7:
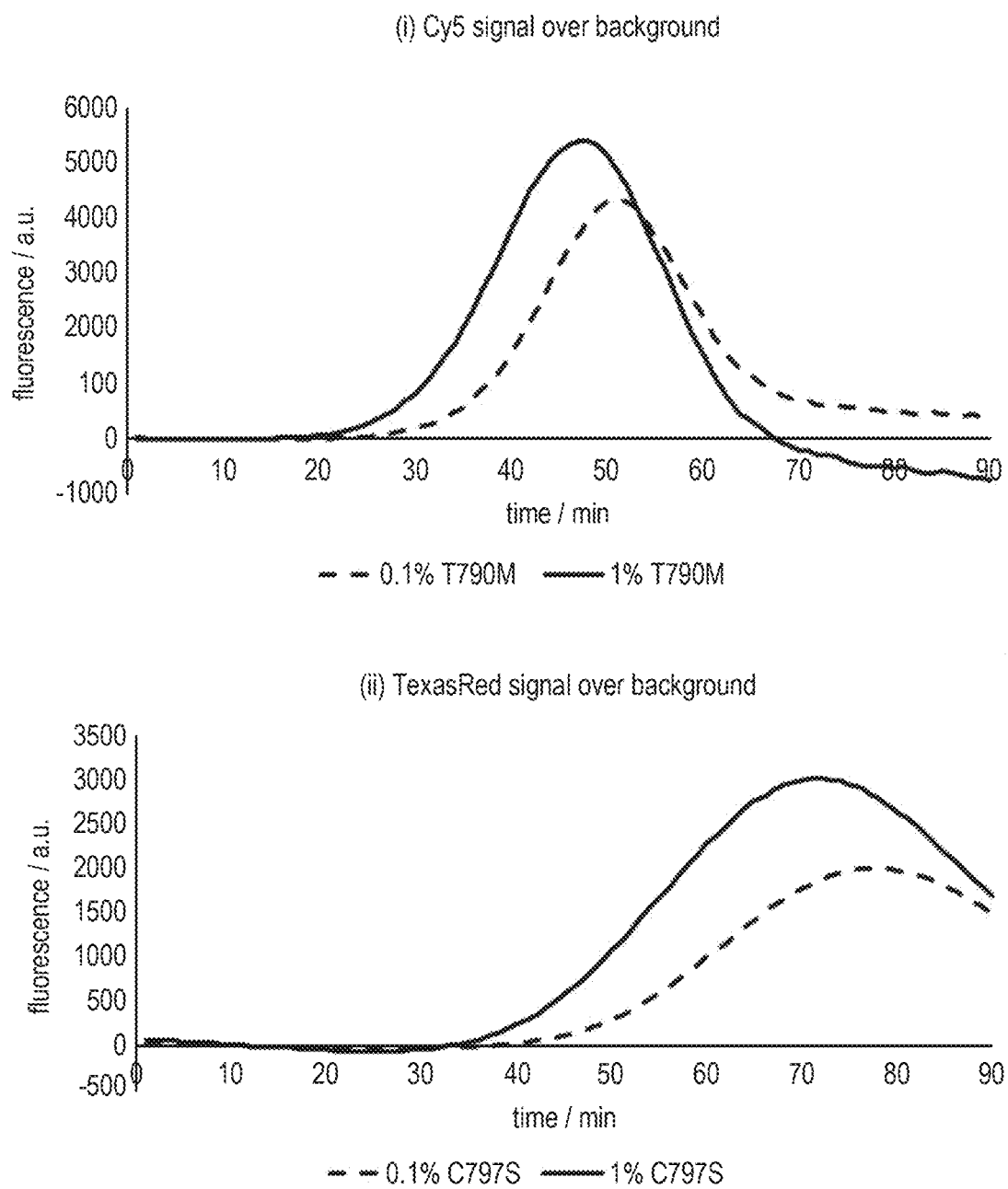
FIG. 7: Signal over wild-type results in two colours for simultaneous detection and identification of the T790M (i) and C797S (ii) EGFR mutations at 0.1% and 1% in a single well as described in Example 7.

As well as 10-plex multiplexed detection using 1 colour, the inventors have also demonstrated two-colour detection in a single well in both the linear and rolling-circle amplification implementations of the current methods (the former using Taqman probes, the latter using stem-loop primers). In this example, samples were prepared containing either the T790M mutation or the C797S mutation at allele fractions of 0%, 0.1% and 0.5%. Following pyrophosphorolysis and subsequent ligation, the samples were subjected to rolling circle or linear PCR amplification using primers or probes specific to the mutation-targeting probes $A_0$ labelled with different fluorophores. The results of the rolling circle amplification using labelled stem-loop primers are shown in FIG. 7 in which it can be seen that signal is generated in the Cy5 detection channel in the presence of the T790M mutation, while signal is observed in the TexasRed channel in samples containing the C797S mutation.

Example 8: Use of Control Probes for Background Signal Calibration

Three samples 1-3 were prepared, each comprising 100 nM final concentration of a synthetic oligonucleotide 1 (SEQ ID NO 24) comprising the wild-type sequence of the L858R mutation region of exon 21 of the human EGFR gene:

5'-CCGCAGCATGTCAAGATCACAGATTTTGGGCTGGCCAAACTGCTGGG

TGCGGAAGAGAAAGAATACCATGCAGAAGGAGG-3'

A synthetic 'mutant' oligonucleotide 2 (SEQ ID NO 25) was prepared, having the following sequence derived from the same region of the EGFR gene and further comprising the L858R mutation:

5'-CCGCAGCATGTCAAGATCACAGATTTTGGGCGGGCCAAACTGCTGGG

TGCGGAAGAGAAAGAATACCATGCAGAAGGAGG-3'

Oligonucleotide 2 was added to samples 2 and 3 at 100 pM and 1 nM final concentrations respectively such that 0.1% of the molecules comprising the L858R mutation site in sample 2 and 1% of those in sample 3 included this mutation. Each sample was then split into two reaction volumes. To the first reaction volume an assay probe oligonucleotide 3 (SEQ ID NO 26) was added at 10 nM final concentration which comprised a 3' end perfectly matching the mutated L858R sequence region while to the second volume a control probe oligonucleotide 4 (SEQ ID NO 27) was added at the same concentration which comprised the same sequence other than in the L858R mutation region in which it comprised a sequence mismatched to both the mutant and wild-type alleles:

Oligonucleotide 3:
5'-PATGTTCGATGAGCTTTGACAATACTTGATCGATGCAGATATAGGAT

GTTGCGACAGTTTGGCCCGCCCAAA-3'

Oligonucleotide 4:
5'-PATGTTCGATGAGCTTTGACAATACTTGATCGATGCAGATATAGGAT

GTTGCGACAGTTTGGCCGGCCCAAA-3'

The reaction volumes were then subjected to pyrophosphorolysis through the addition of 0.6 mM pyrophosphate ion and 37.5 U/mL Mako DNA polymerase and heating to 41° C. for 30 minutes. Following this reaction a splint oligonucleotide 5 (SEQ ID NO 28) was added to each reaction volume at 10 nM final concentration along with 50 U/mL Thermostable Inorganic Pyrophosphatase and 100 U/mL *E. Coli* Ligase and any pyrophosphorolysed probes were circularised through incubation at 37° C. for 10 minutes. The *E. Coli* Ligase was then inactivated through heating to 95° C. for 10 minutes.

Oligonucleotide 5:
5'-TGTCAAAGCTCATCGAACATGCCAAACTGTCGCAAG-3'

Following this, the samples were subjected to exonuclease digestion through addition of Exonuclease III and T5 Exonuclease and incubation at 30° C. for 5 minutes followed by inactivation of the exonucleases through heating to 95° C. for 5 minutes.

To each sample was then added two primer oligonucleotides 6 (SEQ ID NO 29) and 7 (SEQ ID NO 30) at 200 nm final concentration, 0.4 mM dNTPs, 320 U/mL BstLF DNA polymerase and 0.5× final concentration Sybr Green intercalating dye.

Oligonucleotide 6:
5'-TCGCAACATCCTATATCTGC-3'

Oligonucleotide 7:
5'-TGAGCTTTGACAATACTTGA-3'

The samples were incubated at 60° C. for 80 minutes and the fluorescence from the Sybr Green dye in each sample measured once per minute. The results of this incubation are shown in FIG. 8 (*i*), where it can be seen that in the presence of the assay probe the fluorescent signal is dependent on the presence of the L858R mutation, while the signal observed from the control probe is independent of the presence of this mutation and closely matches the signal observed from the probe in the absence of the mutation. FIG. 8 (*ii*) shows the result of subtraction of the control probe signal from the assay probe signal for each of the three samples. Quantitative detection of the L858R mutation down to 0.1% allele fraction without the use of reference samples is thus enabled through this technique.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

It will further be appreciated by those skilled in the art that although the invention has been described by way of example with reference to several embodiments, it is not limited to the disclosed embodiments and that alternative embodiments could be constructed without departing from the scope of the invention as defined in the appended claims.

The invention claimed is:

1. A method of detecting a target polynucleotide sequence in a nucleic acid analyte, the method comprising:
   a. annealing the analyte to a single-stranded probe oligonucleotide $A_0$ to create a first intermediate product which is at least partially double-stranded and in which the 3' end of $A_0$ forms a double-stranded complex with the target polynucleotide sequence;
   b. pyrophosphorolysing the first intermediate product with a pyrophosphorolysing enzyme in the 3'-5' direction from the 3' end of $A_0$ to create partially digested strand $A_1$ and the analyte;
   c. (i) annealing $A_1$ to a single-stranded trigger oligonucleotide B and extending the $A_1$ strand in the 5'-3' direction against B; or (ii) circularising $A_1$ through ligation of its 3' and 5' ends; or (iii) ligating the 3' end of $A_1$ to the 5' end of a ligation probe oligonucleotide C; in each case to create an oligonucleotide $A_2$;
   d. priming $A_2$ with at least one single-stranded primer oligonucleotide and creating multiple copies of $A_2$, or multiple copies of a region of $A_2$; and
   e. detecting a signal derived from the multiple copies and inferring therefrom the presence or absence of the target polynucleotide sequence in the analyte.

2. The method of claim 1, wherein c(ii) or c(iii) is employed, and $A_1$ is first extended in the 5'-3' direction prior to ligation.

3. The method of claim 1, wherein the ligation is performed through addition of a further splint oligonucleotide D to which $A_1$ anneals prior to ligation, wherein D comprises an oligonucleotide region complementary to the 3' end of $A_1$ and a region complementary to either the 5' end of oligonucleotide C or to the 5' end of $A_1$.

4. The method of claim 3, wherein the oligonucleotide D is unable to undergo extension against $A_1$ by virtue of either a 3' modification or through a mismatch between the 3' end of D and the corresponding region of $A_1$.

5. The method of claim 1, wherein a reaction mixture produced from step (c) is treated with an exonuclease after step (c) to substantially digest any non-ligated nucleic acid material, and wherein if c(iii) is employed, the oligonucleotide C further comprises a 3' or internal modification protecting it from 3'-5' exonuclease digestion.

6. The method of claim 5, wherein the exonuclease is deactivated prior to step (d).

7. The method of claim 1, wherein c(i) is employed, and B comprises (i) an oligonucleotide region complementary to the 3' end of $A_1$ and (ii) a flanking oligonucleotide region at its 5' end which is not substantially complementary to $A_0$ or the target polynucleotide sequence, and wherein one of the primer oligonucleotides used in step (d) anneals to the extended region of $A_2$.

8. The method of claim 1, wherein the probe oligonucleotide $A_0$ has a 5' end which is resistant to exonucleolysis and wherein after steps (a) and (b), a reaction medium produced therefrom is treated with a 5'-3' exonuclease to substantially remove any nucleic acid molecules which are not rendered resistant to this exonucleolysis.

9. The method of claim 1, wherein step (b) is carried out in the presence of a phosphatase.

10. The method of claim 1, wherein steps (a) and (b) are iterated to create multiple copies of partially digested probe $A_1$ from the analyte.

11. The method of claim 1, wherein the pyrophosphorolysis reaction is stopped after step (b) through addition of a pyrophosphatase.

12. The method of claim 1, wherein step (e) comprises detecting a signal derived from the multiple copies using one or more oligonucleotide binding dyes or molecular probes.

13. The method of claim 1, wherein steps (d) and (e) are performed concurrently.

14. The method of claim 13, wherein an increase in signal over time resulting from generation of amplicons in step (d) is used to infer a concentration of the target polynucleotide sequence in the analyte.

15. The method of claim 1, wherein the analyte is single-stranded and prior to step (a), the analyte is derived from a biological sample comprising the analyte by:
 (i) producing amplicons of the analyte by subjecting the biological sample to cycles of amplification; and
 (ii) digesting the product of step (i) with an exonuclease having 5'-3' exonucleolytic activity, wherein one of the primers employed in step (i) includes an exonuclease blocking group.

16. The method of claim 15, wherein step (i) is carried out using deoxyuridine triphosphate instead of deoxythymidine triphosphate and in the presence of UTP-DNA glycolase.

17. The method of claim 1, wherein the analyte is single-stranded and prior to step (a), the analyte is derived from a biological sample comprising the analyte by (i) producing amplicons of the analyte by subjecting the biological sample to cycles of amplification, wherein one of the primers employed is introduced in excess to the other(s).

18. The method of claim 17, wherein the amplification employs a polymerase exhibiting 3'-5' exonuclease activity, wherein after step (i), the product of step (i) is reacted with a proteinase to destroy the polymerase, and wherein the proteinase is then destroyed by heating the product of this reaction.

19. The method of claim 17, wherein the amplification employs a polymerase exhibiting 3'-5' exonuclease activity, wherein after step (i), the product of step (i) is reacted with a proteinase to destroy the polymerase, and wherein the proteinase is then destroyed by heating the product of this reaction.

20. The method of claim 17, wherein step (i) is carried out using deoxyuridine triphosphate instead of deoxythymidine triphosphate and in the presence of UTP-DNA glycolase.

21. The method of claim 1, wherein multiple probes $A_0$ are employed, each selective for a different target polynucleotide sequence and each including an identification region, and wherein the region amplified in step (d) includes this identification region.

22. The method of claim 21, wherein the presence of the target sequences present in the analyte is inferred from the amplicons generated in step (d) through the detection of the identification region(s).

23. The method of claim 22, wherein detection of the identification regions(s) is carried out using molecular probes or through sequencing.

24. The method of claim 23, wherein step (e) further comprises the steps of:
 i. labelling the multiple copies of $A_2$, or the multiple copies of the region of $A_2$ using one or more oligonucleotide fluorescent binding dyes or molecular probes;
 ii. measuring the fluorescent signal of the multiple copies;
 iii. exposing the multiple copies to a set of denaturing conditions; and
 iv. identifying the target polynucleotide sequence in the analyte by monitoring changes in the fluorescent signal of the multiple copies during exposure to the denaturing conditions.

25. The method of claim 21, wherein the different probes $A_0$ comprise a common priming site, allowing a single or single set of primers to be used for amplification in step (d).

26. The method of claim 1, wherein prior to step (a), the analyte is split into multiple reaction volumes, each volume having a different probe oligonucleotide $A_0$ introduced to detect a different target polynucleotide sequence.

* * * * *

UNITED STATES PATENT AND TRADEMARK OFFICE
CERTIFICATE OF CORRECTION

PATENT NO. : 10,961,569 B2
APPLICATION NO. : 16/902666
DATED : March 30, 2021
INVENTOR(S) : Barnaby Balmforth et al.

Page 1 of 1

It is certified that error appears in the above-identified patent and that said Letters Patent is hereby corrected as shown below:

In the Claims

Claim 8, Column 40, Line 58, replace "exonucleolysisand" with --exonucleolysis, and--.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*